United States Patent
Sato

(10) Patent No.: US 10,251,537 B2
(45) Date of Patent: Apr. 9, 2019

(54) MAGNIFYING ENDOSCOPE OPTICAL SYSTEM

(71) Applicant: OLYMPUS CORPORATION, Tokyo (JP)

(72) Inventor: Shinya Sato, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 36 days.

(21) Appl. No.: 14/848,664

(22) Filed: Sep. 9, 2015

(65) Prior Publication Data

US 2017/0347867 A1    Dec. 7, 2017

Related U.S. Application Data

(63) Continuation of application No. PCT/JP2014/071485, filed on Aug. 15, 2014.

(30) Foreign Application Priority Data

Aug. 22, 2013  (JP) .................. 2013-172240

(51) Int. Cl.
*A61B 1/04* (2006.01)
*G02B 23/24* (2006.01)
*G02B 9/36* (2006.01)

(52) U.S. Cl.
CPC .............. *A61B 1/04* (2013.01); *G02B 23/243* (2013.01); *G02B 23/2438* (2013.01); *G02B 9/36* (2013.01)

(58) Field of Classification Search
CPC ........ G02B 13/04; G02B 9/36; G02B 23/243; G02B 15/00–15/28; G02B 13/02;
(Continued)

(56) References Cited

U.S. PATENT DOCUMENTS

2009/0102961 A1* 4/2009 Uzawa ............... G02B 9/10
                                                            348/345
2011/0096407 A1* 4/2011 Ohata ............... G02B 13/18
                                                            359/686

FOREIGN PATENT DOCUMENTS

JP   02-090118    3/1990
JP   06-102453    4/1994
(Continued)

OTHER PUBLICATIONS

International Search Report, dated Oct. 7, 2014, issued in corresponding International Application No. PCT/JP2014/071485.

*Primary Examiner* — Kristina M Deherrera
(74) *Attorney, Agent, or Firm* — Hunton Andrews Kurth LLP

(57) ABSTRACT

A large incident angle of an off-axis principal ray is ensured while a stroke of a moving lens group is kept long, and a size is reduced while a focusing operation in magnification is easy.
A magnifying endoscope optical system provided with a negative single lens cemented to an image pickup device and a moving lens group, capable of switching at least between a normal observation state and a proximity magnifying state can be made by moving the moving lens groups; and the following conditional expression (1) is satisfied:

$$-65 < fr/fw < -2 \qquad (1)$$

where reference character fr denotes a focal distance of the negative lens cemented to the image pickup device, and reference character fw denotes a focal distance of the entire system in the normal observation state (wide angle end).

8 Claims, 26 Drawing Sheets

(58) Field of Classification Search
CPC ... G02B 9/04; G02B 9/00–9/64; A61B 13/04;
A61B 1/04
USPC ................................................ 359/676, 686
See application file for complete search history.

(56) References Cited

FOREIGN PATENT DOCUMENTS

| | | |
|---|---|---|
| JP | 11-125770 | 5/1999 |
| JP | 2007-233036 | 9/2007 |
| JP | 2009-103874 | 5/2009 |
| JP | 2009-294496 | 12/2009 |
| JP | 2011-048086 | 3/2011 |

* cited by examiner

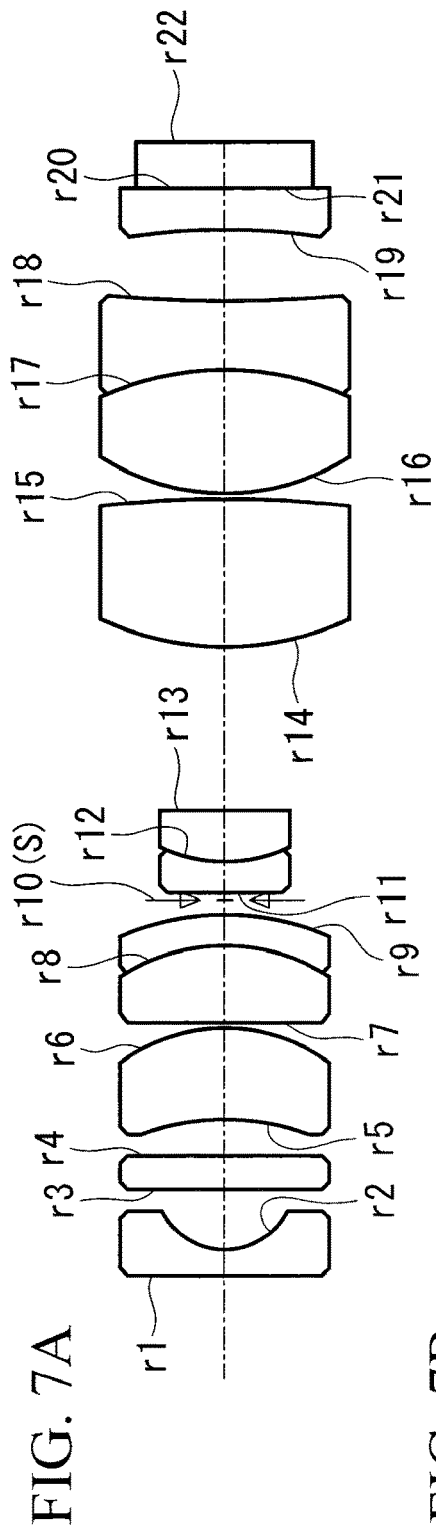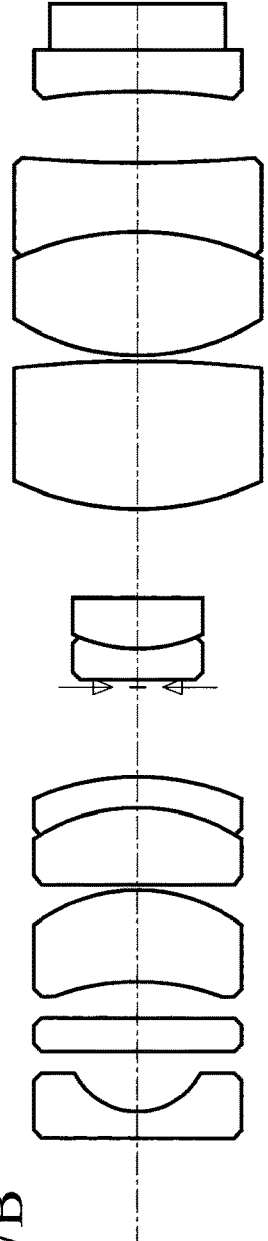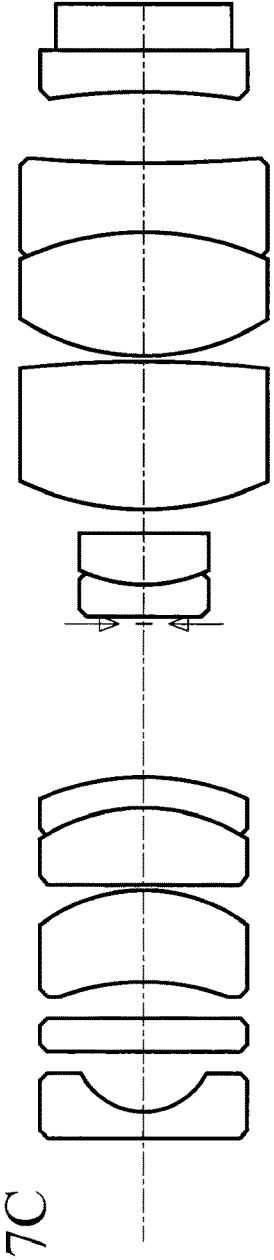
FIG. 7A
FIG. 7B
FIG. 7C

MAGNIFYING ENDOSCOPE OPTICAL SYSTEM

CROSS REFERENCE TO RELATED APPLICATIONS

The present application is a continuation of PCT/JP2014/071485, filed Aug. 15, 2014, and claims priority to Japanese Patent Application No. 2013-172240, filed Aug. 22, 2013, each of which is expressly incorporated herein in its entirety by reference thereto.

TECHNICAL FIELD

The present invention relates to an objective optical system and particularly to a magnifying endoscope optical system applied to a medical endoscope and capable of magnifying observation.

BACKGROUND ART

In the medical endoscope, a demand for an objective optical system capable of magnifying observation for making precise diagnosis of a lesion is increasing.

Examples of the objective optical system having such a magnifying function include an objective optical system capable of switching between a normal observation state and a magnifying observation state by moving a moving lens group along an optical axis disclosed in PTL 1 to PTL 4, for example.

In order to perform magnification in the objective optical system capable of magnifying observation, at least one lens group needs to be moved. In such an objective optical system, in order to facilitate a focusing operation involved in magnification, it is preferable that a stroke of the moving lens group be ensured to be long, and magnification be performed gently.

Moreover, size reduction of an image pickup device has progressed in response to a demand for size reduction of endoscopes, and a small-sized image pickup device with a shading characteristic optimized in accordance with an incident angle of an off-axis principal ray has been provided, and a small-sized endoscope capable of magnifying observation is in demand.

CITATION LIST

Patent Literature

{PTL 1}
Japanese Unexamined Patent Application, Publication No. 2011-48086
{PTL 2}
Japanese Unexamined Patent Application, Publication No. 2009-103874
{PTL 3}
Japanese Unexamined Patent Application, Publication No. Hei 6-102453
{PTL 4}
Japanese Unexamined Patent Application, Publication No. 2007-233036

SUMMARY OF INVENTION

Technical Problem

However, if the stroke of the moving lens group is ensured to be long in the objective optical system, the off-axis ray on an image side from a diaphragm in an optical system becomes high particularly in the normal observation state (wide angle end), and off-axis aberration correction becomes difficult. If a small-sized image pickup device is applied, the stroke of the moving lens group in the objective optical system becomes relatively longer than an image pickup device of a normal size, and thus, the off-axis ray on the image side from the diaphragm also becomes relatively higher, and off-axis aberration correction becomes more difficult.

In particular, since the objective optical systems of PTL 1 to PTL 4 are not provided with a lens having a negative refractive power in the vicinity of an image surface, if the incident angle of the off-axis principal ray is kept appropriately while the stroke of the moving lens group is taken long, off-axis aberration correction becomes difficult, combination with the small-sized image pickup device becomes impossible, and the demand for size reduction of endoscopes cannot be met.

The present invention has been made in view of the aforementioned circumstances and has an object to provide a magnifying endoscope optical system which keeps a stroke of a moving lens group long while it ensures a large incident angle of an off-axis principal ray and is small-sized, and its focusing operation in magnification is easy.

Solution to Problem

In order to achieve the aforementioned object, the present invention provides the following solutions.

An aspect of the present invention provides a magnifying endoscope optical system which is provided with a negative single lens cemented to an image pickup device and a moving lens group, capable of switching at least between a normal observation state and a proximity magnifying state by moving the moving lens group and satisfies the following conditional expression (1):

$$-65 < fr/fw < -2 \qquad (1)$$

where reference character fr denotes a focal distance of the negative lens cemented to the image pickup device, and reference character fw denotes a focal distance of the entire system in the normal observation state (wide angle end).

BRIEF DESCRIPTION OF DRAWINGS

FIGS. 3A, 3B, and 3C are sectional views illustrating the entire constitution of a magnifying endoscope optical system according to an example 1 of the present invention, in which FIG. 3A shows the normal observation state, FIG. 3B shows an interrupted (middle state), and FIG. 3C shows a proximity magnifying state.

FIGS. 7A, 7B, and 7C are sectional views illustrating the entire constitution of a magnifying endoscope optical system according to an example 2 of the present invention, in which FIG. 7A shows the normal observation state, FIG. 7B shows an interrupted (middle state), and FIG. 7C shows a proximity magnifying state.

FIGS. 11A, 11B, and 11C are sectional views illustrating the entire constitution of a magnifying endoscope optical system according to an example 3 of the present invention, in which FIG. 11A shows the normal observation state, FIG. 11B shows an interrupted (middle state), and FIG. 11C shows a proximity magnifying state.

FIGS. 15A, 15B, 15C are sectional views illustrating the entire constitution of a magnifying endoscope optical system according to an example 4 of the present invention, in which FIG. 15A shows the normal observation state, FIG. 15B shows an interrupted (middle state), and FIG. 15C shows a proximity magnifying state.

FIGS. 19A, 19B, and 19C are sectional views illustrating the entire constitution of a magnifying endoscope optical system according to an example 5 of the present invention, in which FIG. 19A shows the normal observation state, FIG. 19B shows an interrupted (middle state), and FIG. 19C shows a proximity magnifying state.

FIGS. 23A, 23B, and 23C are sectional views illustrating the entire constitution of a magnifying endoscope optical system according to an example 6 of the present invention, in which FIG. 23A shows the normal observation state, FIG. 23B shows an interrupted (middle state), and FIG. 23C shows a proximity magnifying state.

DESCRIPTION OF EMBODIMENTS

A magnifying endoscope optical system according to an embodiment of the present invention will be described below by referring to the attached drawings.

Figure 1:
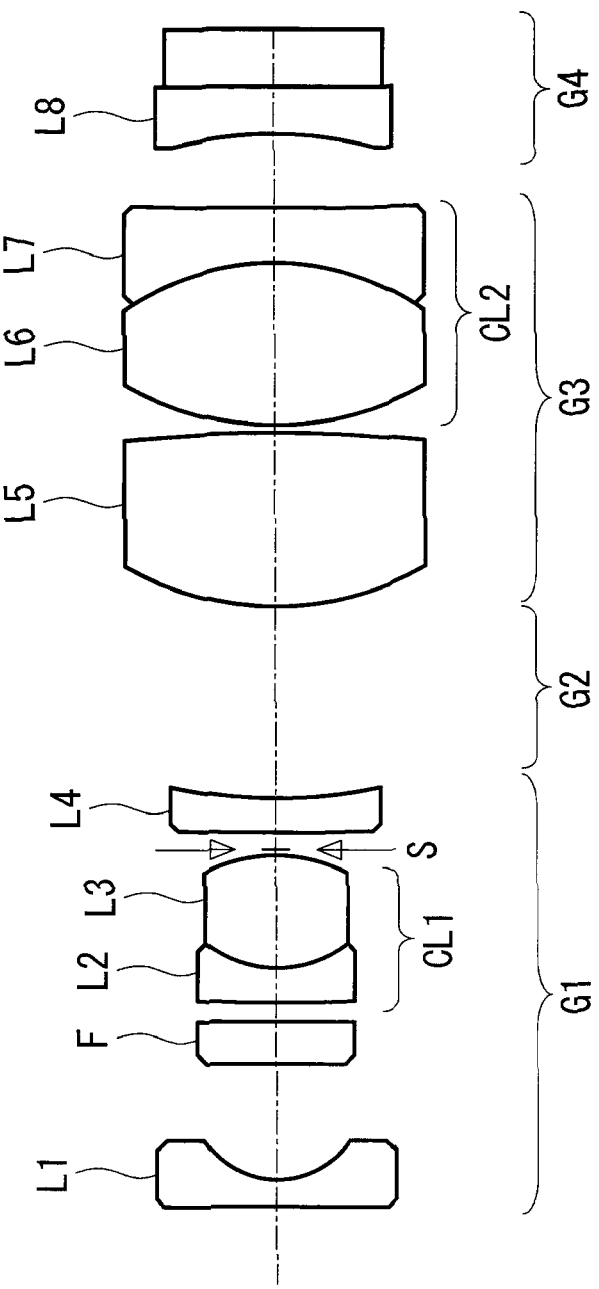
FIG. 1 is a sectional view illustrating the entire constitution of a magnifying endoscope optical system according to an embodiment of the present invention.

FIG. 1 shows a sectional view showing the entire constitution of the magnifying endoscope optical system. As illustrated in FIG. 1, the magnifying endoscope optical system includes a plurality of lens groups, that is, a first lens group G1, a diaphragm S, a second lens group G2, a third lens group G3, and a fourth lens group G4 in order from an object side.

The first lens group G1 includes a first lens L1 which is a plano-concave lens, a parallel planar plate F, and a positive cemented lens CL1 in which a second lens L2 which is a negative meniscus lens and a third lens L3 which is a biconvex lens are cemented, and has a positive refractive power.

The second lens group G2 is formed of a fourth lens L4 which is a plano-concave lens and has a negative refractive power. The second lens group G2 is movable on an optical axis, and by means of movement of the second lens group G2, magnification from a normal observation state to a proximity magnifying state and the like is made possible.

The third lens group G3 includes a fifth lens L5 which is a biconvex lens and a positive cemented lens CL2 in which a sixth lens L6 which is a biconvex lens and a seventh lens L7 which is a biconcave lens are cemented, and has a positive refractive power.

The fourth lens group G4 has a negative refractive power and is an eighth lens L8 cemented to an image pickup device. That is, the eighth lens L8 is a concave-plano lens and is cemented to an image pickup device sealing glass bonded integrally to an image pickup surface.

Image position adjustment is performed within the group interval between the third lens group G3 and the fourth lens group G4.

Moreover, the magnifying endoscope optical system according to the present embodiment is constituted so as to satisfy the following conditional expression (1).

The conditional expression (1) is a condition to correct aberrations favorably by cementing the negative lens to the image pickup device while both a long stroke of a moving group and a large incident angle of an off-axis principal ray are ensured.

$$-65 < fr/fw < -2 \quad (1)$$

where reference character fr denotes a focal distance of the negative lens cemented to the image pickup device, that is, a focal distance of the eighth lens L8, and reference character fw denotes a focal distance of the entire system in the normal observation state (wide angle end).

With size reduction of the image pickup device, in a magnifying optical system, ensuring of the incident angle of the off-axis principal ray is getting more difficult, which easily results in deterioration of image quality.

If the magnifying endoscope optical system satisfies the conditional expression (1), even if the stroke of the moving group is ensured to be long, the large incident angle of the off-axis principal ray can be ensured by an effect of exit pupil positional adjustment of the negative lens cemented to the image pickup device, and off-axis aberrations such as field curvature and astigmatism which are problems in the magnifying optical system can be favorably corrected.

If an upper limit −2 of the conditional expression (1) is exceeded, the refractive power of the negative lens cemented to the image pickup device becomes large, and correction of various aberrations becomes difficult and moreover, since manufacture error sensitivity of eccentricity becomes large, highly accurate cementing is required. If a lower limit −65 of the conditional expression (1) is exceeded, the refractive power of the negative lens cemented to the image pickup device becomes small, and a sufficient effect of the exit pupil positional adjustment cannot be obtained, and ensuring of the large incident angle of the off-axis principal ray becomes difficult.

The magnifying endoscope optical system is constituted to satisfy the conditional expressions (2) to (4).

$$-60 < Rr/R01 < -2 \quad (2)$$

where, reference character Rr denotes a radius of curvature of a surface of the negative eighth lens L8 cemented to the image pickup device on the object side, and reference character R01 denotes a radius of curvature of a surface of the negative first lens L1 on the image side on the side closest to the object.

The conditional expression (2) regulates refractive powers of the first lens L1 and the negative eighth lens L8 cemented to image pickup device. If the upper limit −2 of the conditional expression (2) is exceeded, the radius of curvature of the eighth lens L8 becomes small, which is advantageous for setting of the exit pupil position but disadvantageous for aberration correction. On the other hand, if the lower limit −60 of the conditional expression (2) is exceeded, the radius of curvature of the eighth lens L8 becomes large, which is disadvantageous for arranging the exit pupil close to the image surface and is not favorable in ensuring the large incident angle of the off-axis principal ray.

$$0.15 < Tr/fw < 1.7 \quad (3)$$

where reference character Tr denotes the middle thickness of the negative lens cemented to the image pickup device.

The conditional expression (3) regulates the middle thickness of the negative eighth lens L8 cemented to the image pickup device and the focal distance of the normal observation state (wide angle end). If the upper limit 1.7 of the conditional expression (3) is exceeded, the middle thickness of the negative eighth lens L8 becomes large, which is disadvantageous for the exit pupil positional adjustment, and moreover, the entire length becomes large, which is not preferable for size reduction. On the other hand, if the lower limit 0.15 of the conditional expression (3) is exceeded, the middle thickness of the eighth lens L8 becomes small, and defects such as a crack can easily occur in the lens, which is not preferable.

$$5 < fr/f01 < 68 \quad (4)$$

where, reference character f01 denotes the focal distance of the negative first lens L1.

The conditional expression (4) regulates the refractive powers of the first lens L1 and the negative eighth lens L8 cemented to the image pickup device. If the upper limit 68 of the conditional expression (4) is exceeded, the refractive power of the eighth lens L8 becomes small, which is disadvantageous for the exit pupil positional adjustment. On the other hand, if the lower limit 5 of the conditional expression (4) is exceeded, the refractive power of the eighth lens L8 becomes large, and though it is advantageous for the exit pupil positional adjustment, it is disadvantageous for the aberration correction.

If (4)' or (4)" is applied instead of the aforementioned conditional expression (4), it is further preferable:

$$6.5 < fr/f01 < 35 \quad (4)'$$

$$7.5 < fr/f01 < 15 \quad (4)''$$

Moreover, the magnifying endoscope optical system according to the present embodiment is constituted to satisfy the following conditional expression (5) to conditional expression (7):

$$1.2 < dm/fw < 2.4 \quad (5)$$

$$0.9 < f4/f2 < 9.5 \quad (6)$$

$$-0.6 < \mathrm{expi}(w)/\Sigma d < -0.3 \quad (7)$$

where reference character dm denotes the moving amount of the second group, reference character f4 denotes the focal distance of the fourth group, reference character f2 denotes the focal distance of the second group, reference character expi(w) denotes the exit pupil position of the maximum image height actual ray in the normal observation state (wide angle end), and reference character Σd denotes the entire length of the optical system.

By constituting as above, a simple magnification optical system performing magnification and focusing by moving only the negative second lens group on the optical axis can be realized.

In the magnifying endoscope optical system, in order to facilitate the focusing operation in magnification and to provide excellent operability to the operator, a change in observation power with respect to the moving amount of the moving lens group (hereinafter referred to as magnification sensitivity) needs to be made small so as to perform magnification gently. That is, it is important that the refractive power of the moving lens group is made a proper value, and the stroke is ensured to be long.

The conditional expression (5) regulates a stroke of the moving lens group. If the upper limit 2.4 of the conditional expression (5) is exceeded, the stroke of the moving group becomes too long, and the ray height of the third group becomes large, whereby it becomes difficult to ensure the large incident angle of the off-axis principal ray. If the lower limit 1.2 of the conditional expression (5) is exceeded, the stroke of the moving group becomes small, whereby the magnification sensitivity becomes large, which is not favorable in view of operability.

The conditional expression (6) regulates the refractive powers of the second lens group G2 and the fourth lens group G4. If the refractive powers are deviated from this range, both the long stroke of the second lens group G2 which is the moving group and the large incident angle of the off-axis principal ray cannot be realized easily.

That is, if the upper limit 9.5 of the conditional expression (6) is exceeded, the refractive power of the second group becomes large, and it is disadvantageous for ensuring the long stroke of the moving group. On the other hand, if the lower limit 0.9 of the conditional expression (6) is exceeded, the refractive power of the second group becomes small, and the stroke of the moving group becomes too long, which is disadvantageous for size reduction and moreover, disadvantageous for ensuring the large incident angle of the off-axis principal ray.

If the conditional expression (6)' or the conditional expression (6)" is applied instead of the aforementioned conditional expression (6), it is further preferable:

$$0.95 < f4/f2 < 6.8 \tag{6}'$$

$$1.05 < f4/f2 < 2.4 \tag{6}''$$

The conditional expression (7) regulates the exit pupil arrangement. If the upper limit −0.3 of the conditional expression (7) is exceeded, though it is advantageous for obtaining the large incident angle of the off-axis principal ray, the refractive power of the fourth lens group G4 can become large easily, which is disadvantageous for aberration correction. On the other hand, if the lower limit −0.6 of the conditional expression (7) is exceeded, the exit pupil position goes away from the image surface, which is disadvantageous for obtaining the large incident angle of the off-axis principal ray.

The magnifying endoscope optical system is constituted so as to satisfy the following conditional expression (8):

$$-25 < f4/f1 < -2 \tag{8}$$

where reference character f1 denotes the focal distance of the first group.

The conditional expression (8) regulates refractive powers of the fourth lens group G4 and the first lens group G1. If the upper limit −2 of the conditional expression (8) is exceeded, the refractive power of the fourth group becomes large, which is disadvantageous for aberration correction. On the other hand, if the lower limit −25 of the conditional expression (8) is exceeded, the refractive power of the fourth group becomes small, the sufficient effect of the exit pupil positional adjustment cannot be obtained, and ensuring of the large incident angle of the off-axis principal ray becomes difficult.

If the conditional expression (8)' or the conditional expression (8)" is applied instead of the aforementioned conditional expression (8), it is further preferable:

$$-16 < f4/f1 < -2.3 \tag{8}'$$

$$-5.5 < f4/f1 < -2.5 \tag{8}''$$

Moreover, the magnifying endoscope according to the present embodiment is preferably constituted so as to satisfy the following conditional expression (9):

$$13.5 < \Sigma d/IH < 19 \tag{9}$$

where reference character IH denotes the maximum image height.

If size reduction of the magnifying endoscope optical system further progresses and its entire length is reduced, an edge thickness or the middle thickness of the lens cannot be ensured easily, and defects such as split or a crack can occur easily. Thus, by satisfying the conditional expression (9), workability of the lens can be ensured.

That is, the conditional expression (9) is a condition for ensuring the workability of the lens. If the upper limit 19 of the conditional expression (9) is exceeded, the entire length becomes large to the image height, which is disadvantageous for size reduction. On the other hand, if the lower limit 13.5 of the conditional expression (9) is exceeded, the entire length becomes small to the image height, the edge thickness and middle thickness of each lens become small, and defects such as split or a crack can easily occur, which is not preferable.

The magnifying endoscope according to the present embodiment is preferably constituted so as to satisfy the following conditional expression (10):

$$6.7 < \Sigma d\_R/fw < 7.8 \tag{10}$$

where reference character $\Sigma d\_R$ denotes a length from an end on a moving group image side to an image surface in the proximity magnifying state (telescopic end).

In the optical system capable of magnification, at least one lens needs to be moved, and a mechanism for moving the lens is needed. As a mechanism for moving the lens, an actuator or the like connected to a lens frame for holding the moving lens groups and giving a driving force to this lens frame can be cited, for example.

If a lens system is made smaller, it is difficult to reduce the size of the mechanism for moving the lens by the same coefficient times, and components for moving the lens tends to be relatively larger than a large-sized lens system.

That is, in a high-performance magnifying endoscope optical system having the whole angle of view of 120° or more in the normal observation state (wide angle end), the conditional expression (10) is a condition for allowing a space in which components for moving the lens are arranged to be ensured easily. If the upper limit 7.8 of the conditional expression (10) is exceeded, it is advantageous for arranging the components for moving the lens, but the entire length becomes long, which is disadvantageous for size reduction. On the other hand, if the lower limit 6.7 of the conditional expression (10) is exceeded, arrangement of components for moving the lens becomes difficult, which is not preferable.

The magnifying endoscope according to the present embodiment is preferably constituted so as to satisfy the following conditional expression (11):

$$-8 < f2/fw < -5 \tag{11}$$

where reference character f2 is the focal distance of the second group.

The conditional expression (11) regulates the refractive power of the second lens group G2. If the upper limit −5 of the conditional expression (11) is exceeded, the refractive power of the second lens group G2 becomes large, and it is disadvantageous for ensuring a long stroke. On the other hand, if the lower limit −8 of the conditional expression (12) is exceeded, the stroke becomes too long, and the ray height of the third lens group G3 becomes large, which is disadvantageous for aberration correction.

The magnifying endoscope according to the present embodiment is preferably constituted so as to satisfy the following conditional expression (12):

$$2.7 < f3/fw < 4.2 \tag{12}$$

The conditional expression (12) regulates the refractive power of the third lens group G3. If the upper limit 4.2 of the conditional expression (12) is exceeded, the refractive power of the third lens group G3 becomes small, and it is disadvantageous for ensuring a large incident angle of the off-axis principal ray. On the other hand, if the lower limit 2.7 of the conditional expression (12) is exceeded, the refractive power of the third lens group G3 becomes large, which is disadvantageous for aberration correction.

The magnifying endoscope according to the present embodiment is preferably constituted so as to satisfy the following conditional expression (13):

$$-1.1 < f01/fw < -0.87 \tag{13}$$

The conditional expression (13) regulates the refractive power of the first lens L1. If the upper limit −0.87 of the conditional expression (13) is exceeded, the refractive power of the first lens L1 becomes large, and correction of various aberrations becomes difficult. On the other hand, if the lower limit −1.1 of the conditional expression (13) is exceeded, the diameter of the first lens L1 can become large easily, which is disadvantageous for size reduction.

The magnifying endoscope according to the present embodiment is preferably constituted so as to satisfy the following conditional expression (14):

$$-90 < f4/Bf < -2 \qquad (14)$$

where reference character Bf denotes the group interval between the third lens group G3 and the fourth lens group G4.

The conditional expression (14) regulates the refractive power of the fourth lens group G4 and the group interval between the third lens group G3 and the fourth lens group G4. If the upper limit −2 of the conditional expression (14) is exceeded, the group interval between the third lens group G3 and the fourth lens group G4 becomes large, which is disadvantageous for size reduction. On the other hand, if the lower limit −90 of the conditional expression (14) is exceeded, the group interval between the third lens group G3 and the fourth lens group G4 becomes small, and an interval required for the image positional adjustment cannot be ensured, which is not preferable.

The magnifying endoscope according to the present embodiment is preferably constituted so as to satisfy the following conditional expression (15):

$$-20 < f4/f3 < -1.6 \qquad (15)$$

The conditional expression (15) regulates the refractive powers of the fourth lens group G4 and the third lens group G3. If the upper limit −1.8 of the conditional expression (15) is exceeded, the refractive power of the fourth lens group G4 becomes large, which is disadvantageous for aberration correction. On the other hand, if the lower limit −20 of the conditional expression (15) is exceeded, the refractive power of the fourth lens group G4 becomes small, the sufficient effect of the exit pupil positional adjustment cannot be obtained, and ensuring of the large incident angle of the off-axis principal ray becomes difficult.

The magnifying endoscope according to the present embodiment is preferably constituted so as to satisfy the following conditional expression (16):

$$-0.67 < f3/f2 < -0.42 \qquad (16)$$

where reference character f3 denotes the focal distance of the third lens group G3.

The conditional expression (16) regulates the refractive powers of the third lens group G3 and the second lens group G2. If the upper limit −0.42 of the conditional expression (16) is exceeded, the refractive power of the second lens group G2 becomes small, and the stroke becomes long. That is, the entire length becomes long and moreover, the ray height of the third lens group G3 becomes large, which is disadvantageous for aberration correction. On the other hand, if the lower limit −0.67 of the conditional expression (16) is exceeded, the refractive power of the third lens group G3 becomes small, and a back focus of the optical system becomes long, which is disadvantageous for size reduction.

The magnifying endoscope according to the present embodiment is preferably constituted so as to satisfy the following conditional expression (17):

$$1.2 < f3/f1 < 1.65 \qquad (17)$$

The conditional expression (17) regulates the refractive powers of the third lens group G3 and the first lens group G1. If the upper limit 1.65 of the conditional expression (17) is exceeded, the refractive power of the third lens group G3 becomes small, a Petzval sum becomes large, and correction of field curvature becomes difficult. On the other hand, if the lower limit 1.2 of the conditional expression (17) is exceeded, the refractive power of the first lens group G1 becomes small, and correction of spherical aberration becomes insufficient, which is not preferable.

The magnifying endoscope according to the present embodiment is preferably constituted so as to satisfy the following conditional expression (18):

$$3.7 < f2/f1 < -2 \qquad (18)$$

The conditional expression (18) regulates the refractive powers of the second lens group G2 and the first lens group G1. If the upper limit −2 of the conditional expression (18) is exceeded, the refractive power of the second group becomes large as compared with the refractive power of the first group, and fluctuation of chromatic aberration by movement of the second lens group G2 becomes large. On the other hand, if the lower limit −3.7 of the conditional expression (18) is exceeded, the refractive power of the first lens group G1 becomes large, and a generation amount of the spherical aberration becomes large.

As described above, according to the present embodiment, only the second lens group G2 moves on the optical axis, and magnification and focusing are performed so that simple constitution with eight lenses in four groups in the entire system can be taken. That is, while the stroke of the second lens group G2 which is the moving lens group is kept long, the large incident angle of the off-axis principal ray is ensured, whereby the size of the magnifying endoscope optical system can be reduced with the focusing operation in magnification remaining easy. The first lens may be a negative meniscus lens with the concave surface directed to the image surface side.

(Variation)

Moreover, as a variation, the magnifying endoscope optical system may be constituted as follows.

Figure 2:
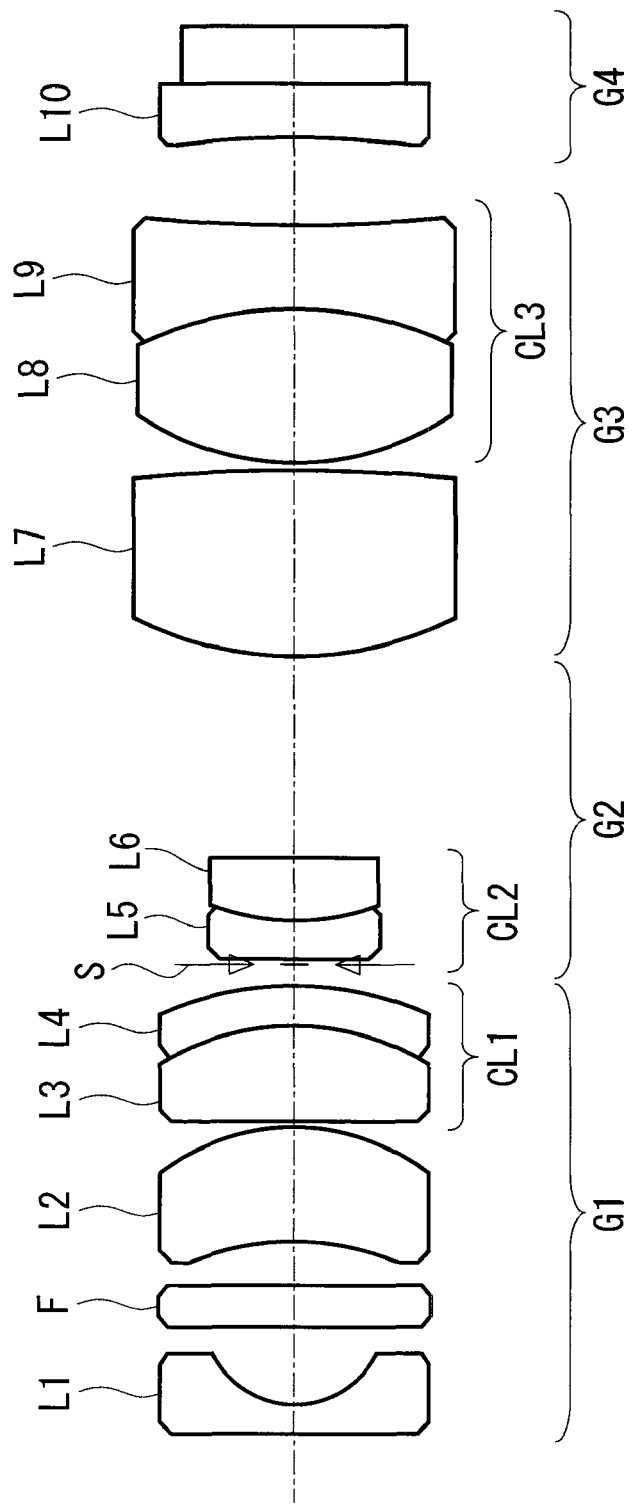
FIG. 2 is a sectional view illustrating the entire constitution of a magnifying endoscope optical system according to a variation of the embodiment of the present invention.

The magnifying endoscope optical system according to the variation includes, as illustrated in FIG. 2, the first lens group G1, the diaphragm S, the second lens group G2, the third lens group G3, and the fourth lens group G4 in order from the object side, and each lens group is constituted as follows.

The first lens group G1 includes the first lens L1 which is a plano-concave lens with a concave surface directed to the image surface side, a second lens L2 which is a positive meniscus lens with a convex surface directed to the image surface side, and a positive cemented lens CL1 in which the third lens L3 which is a positive lens and the fourth lens L4 which is a negative lens are cemented in order of positive and negative.

The second lens group G2 includes a negative cemented lens CL2 in which the fifth lens L5 which is a plano-concave lens with the concave surface directed to the image surface side and the sixth lens L6 which is a positive lens are cemented.

The third lens group G3 includes the seventh lens L7 which is a positive lens and a positive cemented lens CL3 in which the eighth lens L8 which is a positive lens and a ninth lens L9 which is a negative lens are cemented in order of positive and negative.

The fourth lens group G4 includes a tenth lens L10 which is a concave-plano lens with the concave surface directed to the object side. The tenth lens L10 is cemented to an image pickup device sealing glass integrally bonded to an image pickup surface.

Image positional adjustment is made within the group interval between the third lens group G3 and the fourth lens group G4, the second lens group G2 and the diaphragm S arranged on the object side of the second lens group G2 are integrally moved on the optical axis, and magnification and focusing are performed so that constitution of ten lenses in four groups in the entire system resistant to a manufacturing error of eccentricity can be taken. The first lens may be a negative meniscus lens with the concave surface directed to the image surface side.

The magnifying endoscope optical system according to the present variation is also constituted so as to satisfy the aforementioned conditional expression (1) to the conditional expression (8) and is preferably constituted so as to satisfy the conditional expression (9) to the conditional expression (18).

The diaphragm S can be arranged on the image side of the second lens group G2. In this case, the second lens group and the diaphragm S are integrally moved on the optical axis, and by performing focusing and magnification, there is an effect of making the ray height of the third lens group G3 small. That is, the lens diameter of the third lens group G3 can be made small, and if the lens diameter of the third lens group G3 is to be made small for constitution of lens frame components and an actuator, it is a great merit.

Example

Subsequently, Example 1 to Example 6 of the objective optical system according to any one of the aforementioned embodiments will be described by referring to FIGS. 3A to 26. In lens data described in each example, reference character r denotes a radius of curvature (unit: mm), reference character d denotes spacing (mm), reference character Ne denotes a refractive index to an e line, and reference character vd denotes an abbe number to a d line.

Example 1

Figure 3A:
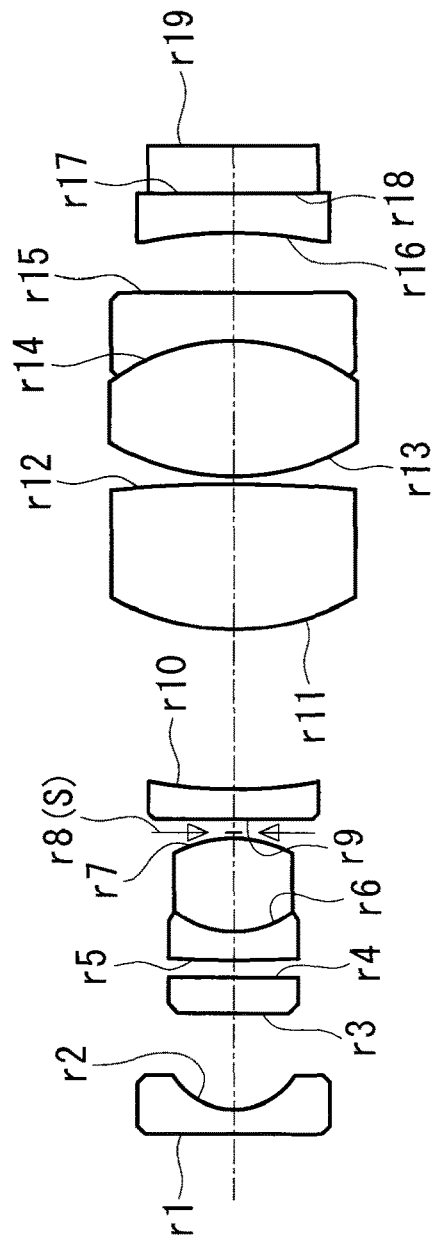
Figure 3B:
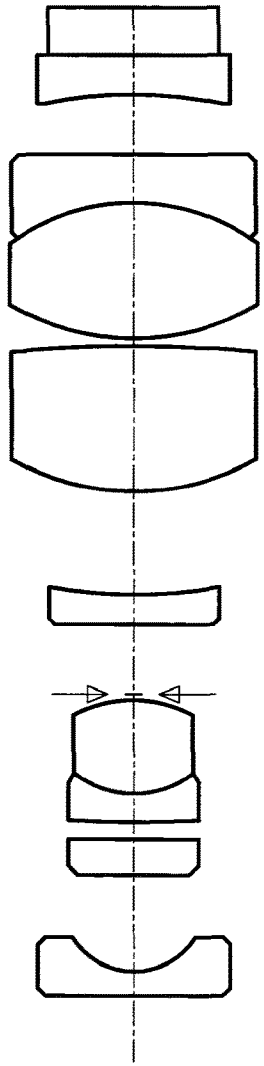
Figure 3C:
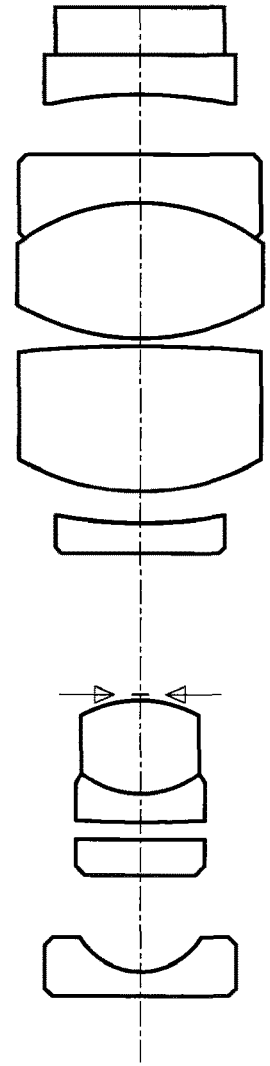

A sectional view showing the entire constitution of the magnifying endoscope optical system according to Example 1 of the present invention is illustrated in FIGS. 3A, 3B, and 3C.

The magnifying endoscope optical system according to Example 1 is constituted of the first lens group having a positive refractive power, the second lens group having a negative refractive power, the third lens group having a positive refractive power, and the fourth lens group having a negative refractive power in order from the object side. The diaphragm is fixed to the object side of the second lens group.

Magnification from the normal observation state (wide angle end) to the proximity magnifying state (telescopic end) and focusing are performed by moving the second lens group on the optical axis to the image side. That is, by moving the second lens group along the optical axis, magnification and focusing are performed.

Moreover, as illustrated in FIGS. 3A, 3B, and 3C, the first lens group is constituted of a plano-concave lens, a parallel planar plate, and a positive cemented lens in which a negative meniscus lens and a biconvex lens are cemented, the second lens group is constituted of a plano-concave lens, the third lens group is constituted of a biconvex lens and a positive cemented lens in which a biconvex lens and a biconcave lens are cemented, and the fourth lens group is constituted of a concave-plano lens. The concave-plano lens of the fourth lens group, the image pickup device sealing glass, and the image pickup surface are integrally bonded to each other.

Example 1 satisfies the conditional expression (1) to the conditional expression (8) and as a result, the long stroke of the moving group and the large incident angle of the off-axis principal ray are ensured.

To the parallel planar plate, a filter for shutting off a specific wavelength such as a YAG laser at 1060 nm, a semiconductor laser at 810 nm or a light beam in a near-infrared region can be applied.

Figure 4:
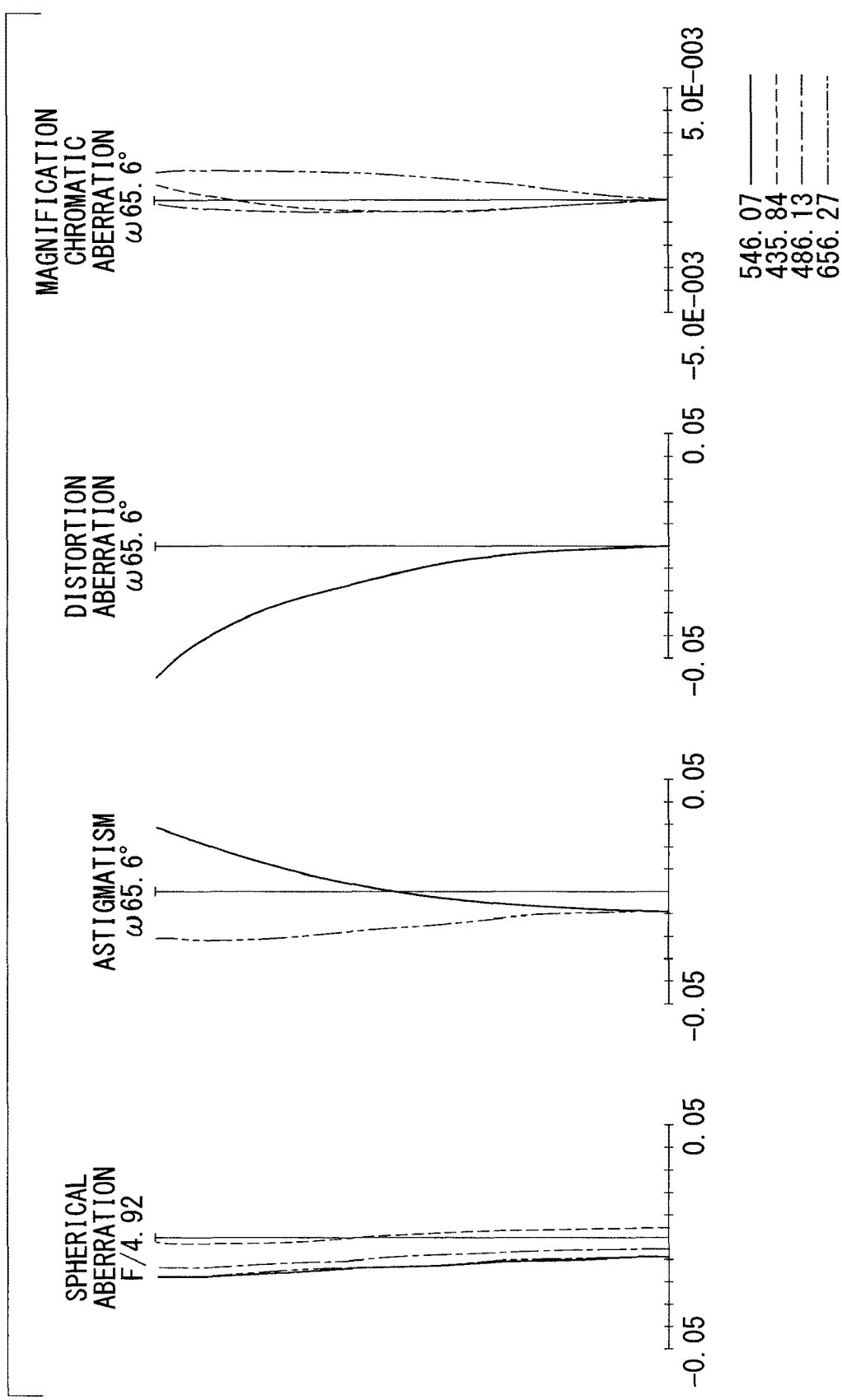
FIG. 4 is an aberration diagram of a normal observation state (wide angle end) in the magnifying endoscope optical system according to the example 1 of the present invention.
Figure 5:
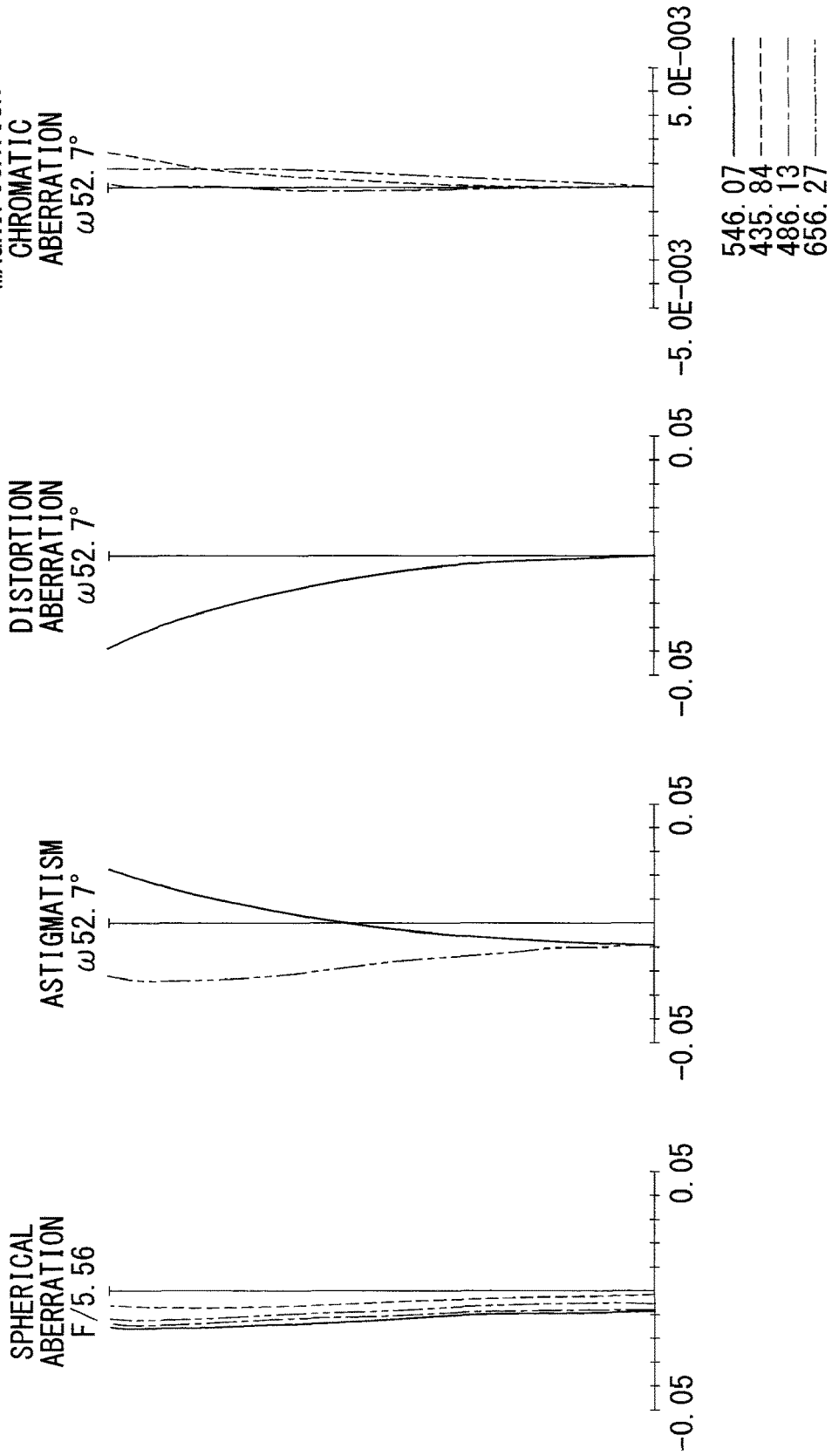
FIG. 5 is an aberration diagram of a middle state in the magnifying endoscope optical system according to the example 1 of the present invention.
Figure 6:
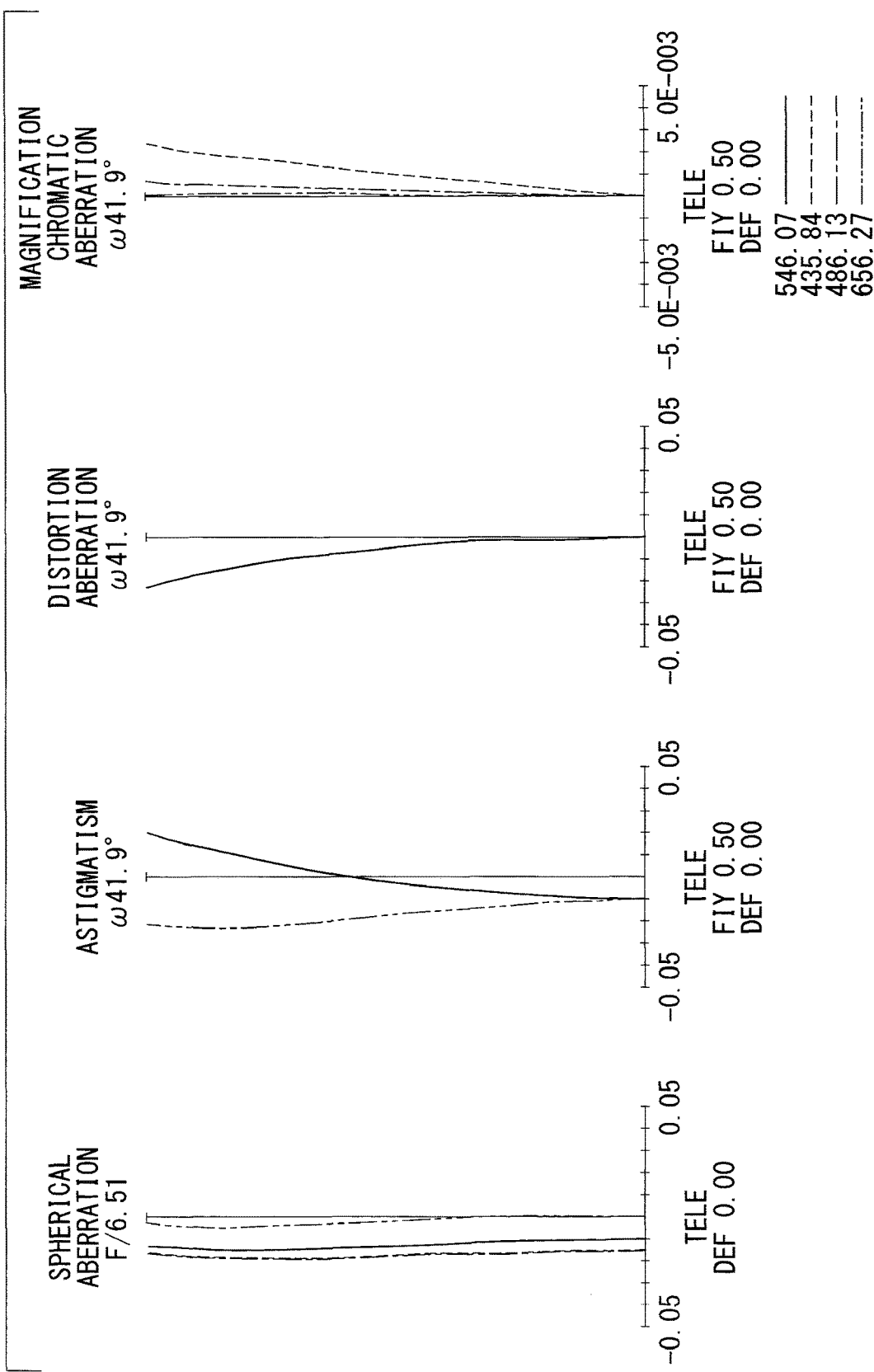
FIG. 6 is an aberration diagram of a proximity magnifying state (telescopic end) in the magnifying endoscope optical system according to the example 1 of the present invention.

Aberration diagrams of the magnifying endoscope optical system according to Example 1 are illustrated in FIGS. 4 to 6, respectively, and their lens data are shown below.

Lens Data

| Surface number | r | d | Ne | vd |
|---|---|---|---|---|
| 0 (Object surface) | ∞ | D0 | | |
| 1 | ∞ | 0.1938 | 1.88814 | 40.78 |
| 2 | 0.4970 | 0.7845 | | |
| 3 | ∞ | 0.2907 | 1.52300 | 65.13 |
| 4 | ∞ | 0.1248 | | |
| 5 | 12.2699 | 0.2422 | 1.88815 | 40.76 |
| 6 | 0.6584 | 0.7503 | 1.72341 | 50.23 |
| 7 | −0.9927 | 0.0484 | | |
| 8 (Diaphragm) | ∞ | D1 | | |
| 9 | ∞ | 0.2422 | 1.82017 | 46.62 |
| 10 | 2.8875 | D2 | | |
| 11 | 1.7244 | 1.1890 | 1.48915 | 70.23 |
| 12 | −8.4378 | 0.0480 | | |
| 13 | 1.6342 | 1.1030 | 1.59143 | 61.14 |
| 14 | −1.4281 | 0.3817 | 1.93429 | 18.90 |
| 15 | 36.6777 | 0.5082 | | |
| 16 | −2.6189 | 0.3198 | 1.51825 | 64.14 |
| 17 | ∞ | 0.0097 | 1.51500 | 64.00 |
| 18 | ∞ | 0.3876 | 1.50700 | 63.26 |
| 19 | ∞ | | | |

Various Data

| | Normal observation state (wide angle end) | Middle state | Proximity magnifying state (telescopic end) |
|---|---|---|---|
| D0 | 9.6899 | 4.3605 | 2.3256 |
| D1 | 0.1163 | 0.5597 | 1.1531 |
| D2 | 1.2984 | 0.8550 | 0.2616 |
| fl | 0.568 | 0.632 | 0.711 |
| Fno | 4.92 | 5.56 | 6.51 |

Example 2

A sectional view showing the entire constitution of the magnifying endoscope optical system according to Example 2 of the present invention is illustrated in FIGS. 7A, 7B, and 7C.

The magnifying endoscope optical system according to Example 2 is constituted of the first lens group having a positive refractive power, the second lens group having a negative refractive power, the third lens group having a positive refractive power, and the fourth lens group having a negative refractive power in order from the object side. The diaphragm is arranged on the object side of the second lens group.

In the magnifying endoscope optical system according to Example 2, the second lens group moves integrally with the diaphragm on the optical axis to the image side and performs magnification from the normal observation state (wide angle end) to the proximity magnifying state (telescopic end) and focusing. That is, magnification and focusing are performed by moving the second lens group along the optical axis.

The first lens group is constituted of a plano-concave lens, a parallel planar plate, a positive meniscus lens with the convex surface directed to the image side, and a positive cemented lens in which a positive meniscus lens with the convex surface directed to the image side and a negative meniscus lens with the convex surface directed to the image side are cemented, the second lens group is constituted of a negative cemented lens in which a plano-concave lens and a positive meniscus lens with the convex surface directed to the object side are cemented, the third lens group is constituted of a biconvex lens and a positive cemented lens in which a biconvex lens and a biconcave lens are cemented, and the fourth lens group is constituted of a concave-plano lens. The concave-plano lens of the fourth lens group, the image pickup device sealing glass and the image pickup surface are integrally bonded to each other.

Example 2 satisfies the conditional expression (1) to the conditional expression (8) and as a result, the long stroke of the moving group and the large incident angle of the off-axis principal ray are ensured.

To the parallel planar plate, a filter for shutting off a specific wavelength such as a YAG laser at 1060 nm, a semiconductor laser at 810 nm or a light beam in a near-infrared region can be applied.

Figure 8:
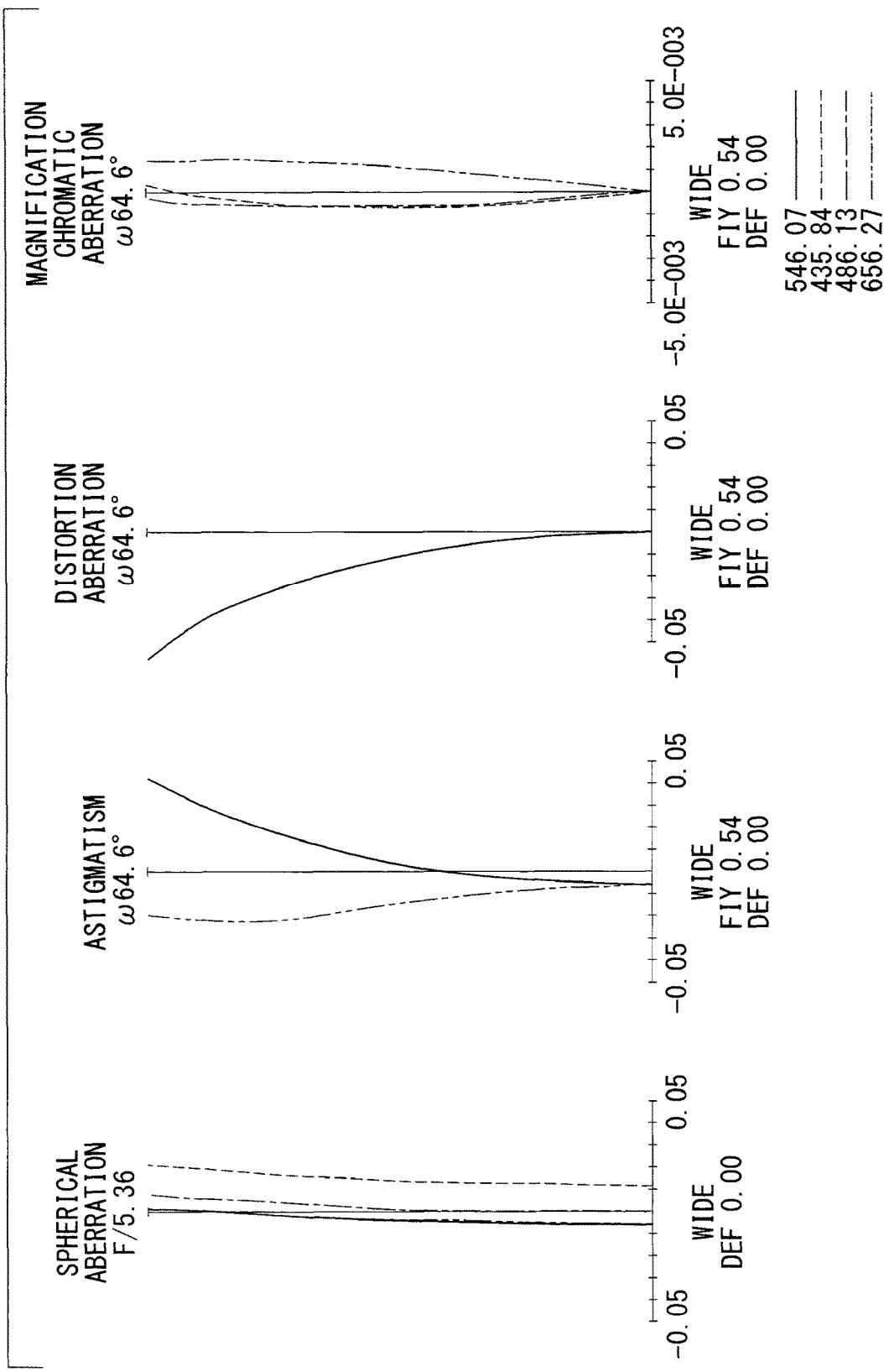
FIG. 8 is an aberration diagram of the normal observation state (wide angle end) in the magnifying endoscope optical system according to the example 2 of the present invention.
Figure 9:
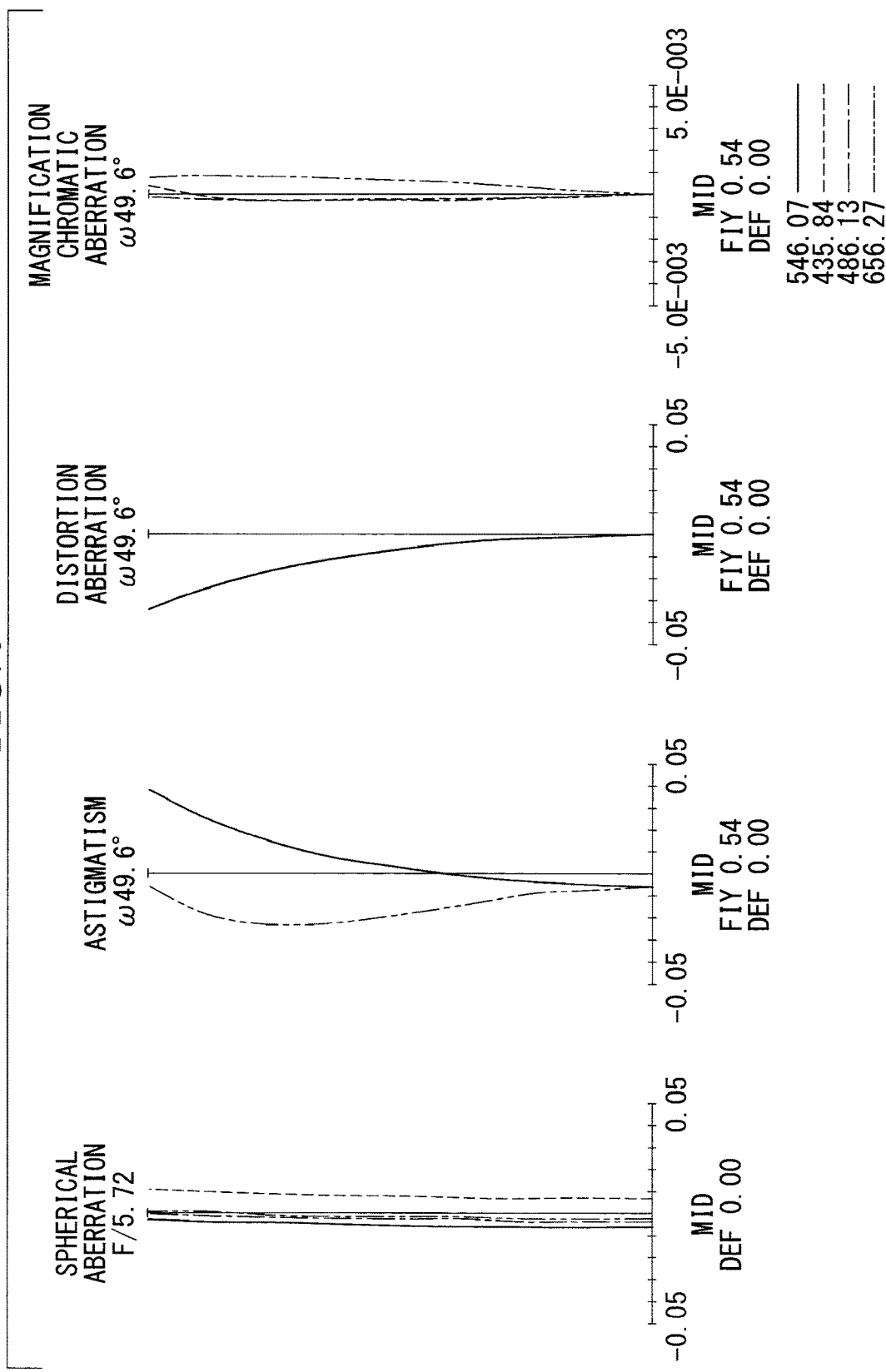
FIG. 9 is an aberration diagram of a middle state in the magnifying endoscope optical system according to the example 2 of the present invention.
Figure 10:
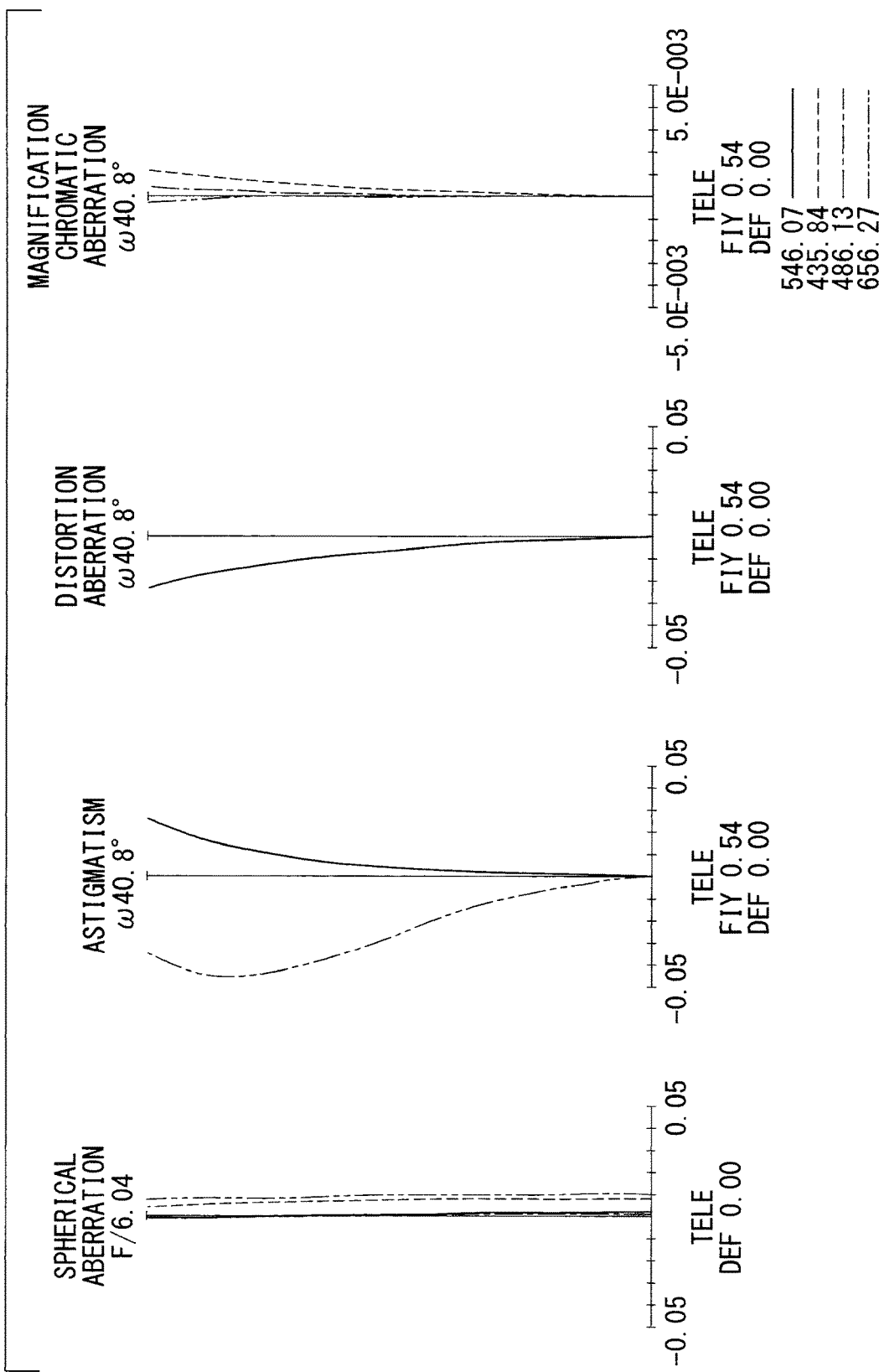
FIG. 10 is an aberration diagram of the proximity magnifying state (telescopic end) in the magnifying endoscope optical system according to the example 2 of the present invention.

Aberration diagrams of the magnifying endoscope optical system according to Example 2 are illustrated in FIGS. 8 to 10, respectively, and their lens data are shown below.

Lens Data

| Surface number | r | d | Ne | vd |
|---|---|---|---|---|
| 0 | ∞ | D0 | | |
| 1 | ∞ | 0.2000 | 1.88815 | 40.76 |
| 2 | 0.5337 | 0.5350 | | |
| 3 | ∞ | 0.2900 | 1.52300 | 65.13 |
| 4 | ∞ | 0.3000 | | |
| 5 | −1.7969 | 0.8058 | 1.59143 | 61.14 |
| 6 | −1.2747 | 0.0523 | | |
| 7 | −32.5151 | 0.6488 | 1.65425 | 58.55 |
| 8 | −1.4567 | 0.2728 | 1.93429 | 18.90 |
| 9 | −1.9015 | D1 | | |
| STO | ∞ | 0.0314 | | |
| 11 | ∞ | 0.2616 | 1.88815 | 40.76 |
| 12 | 1.1847 | 0.4291 | 1.65222 | 33.79 |
| 13 | 15.3335 | D2 | | |
| 14 | 2.1443 | 1.2872 | 1.59143 | 61.14 |
| 15 | −8.4506 | 0.0523 | | |
| 16 | 1.6838 | 1.0779 | 1.48915 | 70.23 |
| 17 | −1.9790 | 0.5756 | 1.93429 | 18.90 |
| 18 | 7.2481 | 0.6309 | | |
| 19 | −4.2687 | 0.3453 | 1.51825 | 64.14 |
| 20 | ∞ | 0.0090 | 1.51500 | 64.00 |
| 21 | ∞ | 0.4100 | 1.50700 | 63.26 |
| 22 | ∞ | | | |

Various Data

| | Normal observation state (wide angle end) | Middle state | Proximity magnifying state (telescopic end) |
|---|---|---|---|
| D0 | 10.45 | 4.2000 | 2.45 |
| D1 | 0.1570 | 0.8020 | 1.3605 |
| D2 | 1.4128 | 0.7678 | 0.2093 |
| Fl | 0.621 | 0.709 | 0.779 |
| Fno | 5.36 | 5.72 | 6.04 |

Example 3

Figures 11A, 11B, 11C:
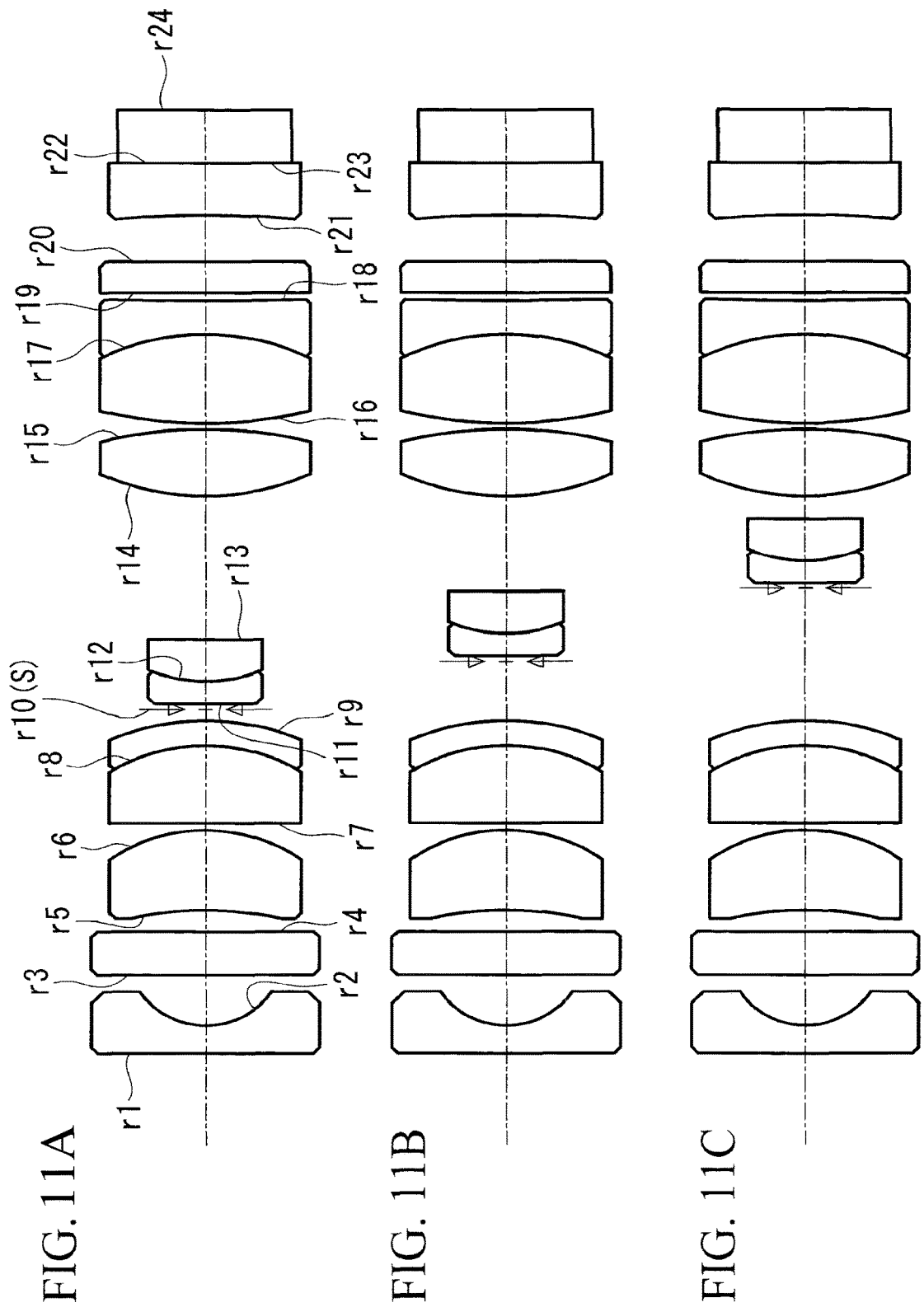

A sectional view showing the entire constitution of the magnifying endoscope optical system according to Example 3 of the present invention is illustrated in FIGS. 11A, 11B, and 11C.

The magnifying endoscope optical system according to Example 3 is constituted of the first lens group having a positive refractive power, the second lens group having a negative refractive power, the third lens group having a positive refractive power, and the fourth lens group having a negative refractive power in order from the object side. The diaphragm is fixed to the object side of the second lens group.

In the magnifying endoscope optical system according to Example 3, the second lens group moves on the optical axis to the image side and performs magnification from the normal observation state (wide angle end) to the proximity magnifying state (telescopic end) and focusing. That is, magnification and focusing are performed by moving the second lens group along the optical axis.

The first lens group is constituted of a plano-concave lens, a parallel planar plate, a positive meniscus lens with the convex surface directed to the image side, and a positive cemented lens in which a biconvex lens and a negative meniscus lens with the convex surface directed to the image side are cemented, the second lens group is constituted of a negative cemented lens in which a plano-concave lens and a biconvex lens are cemented, the third lens group is constituted of a biconvex lens, a positive cemented lens in which a biconvex lens and a biconcave lens are cemented, and a parallel planar plate, and the fourth lens group is constituted of a concave-plano lens. The concave-plano lens of the fourth lens group, the image pickup device sealing glass, and the image pickup surface are integrally bonded to each other.

Example 3 satisfies the conditional expression (1) to the conditional expression (8) and as a result, the long stroke of the moving group and the large incident angle of the off-axis principal ray are ensured.

To the parallel planar plate, a filter for shutting off a specific wavelength such as a YAG laser at 1060 nm, a semiconductor laser at 810 nm or a light beam in a near-infrared region can be applied.

Figure 12:
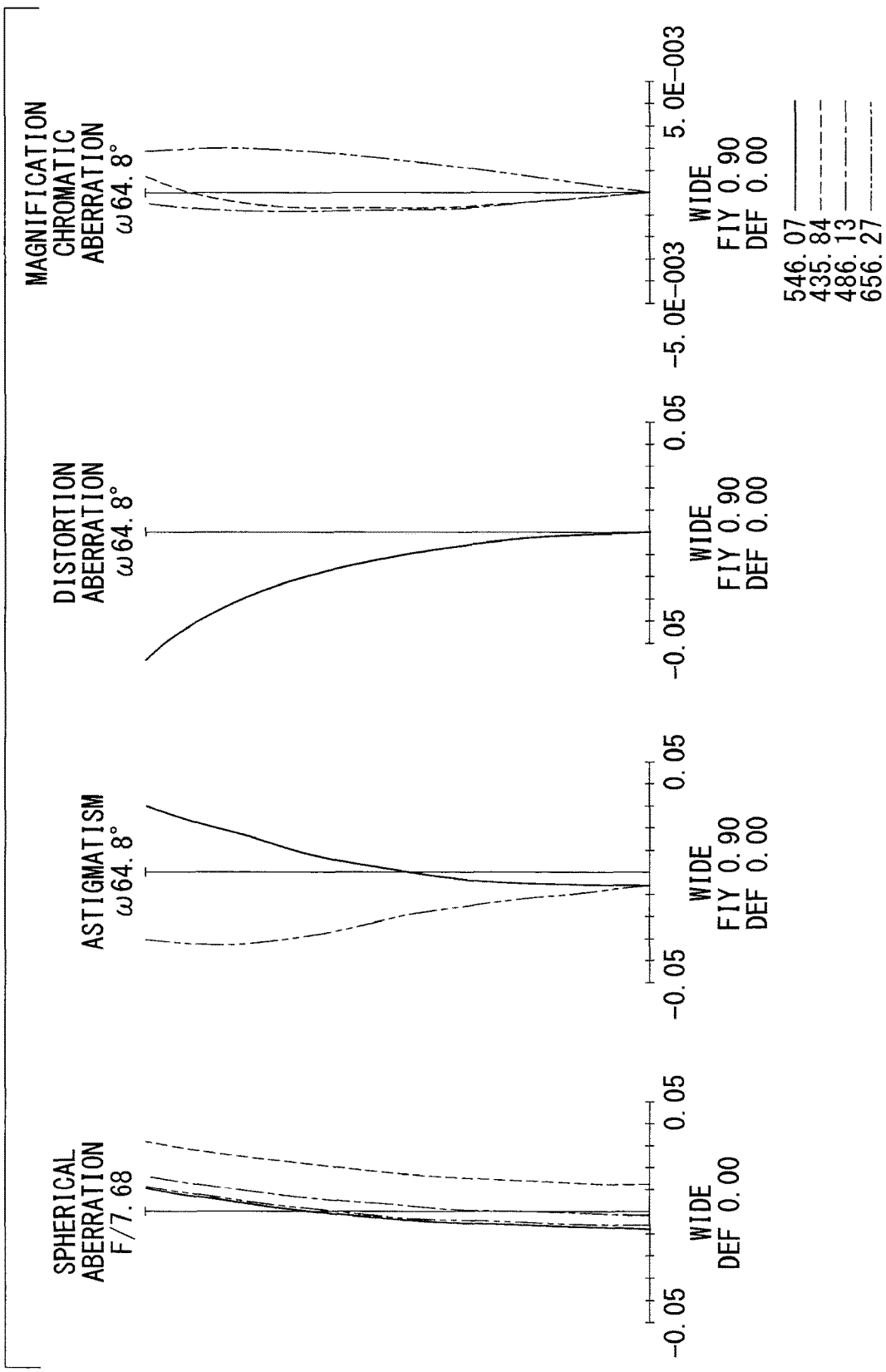
FIG. 12 is an aberration diagram of the normal observation state (wide angle end) in the magnifying endoscope optical system according to the example 3 of the present invention.
Figure 13:
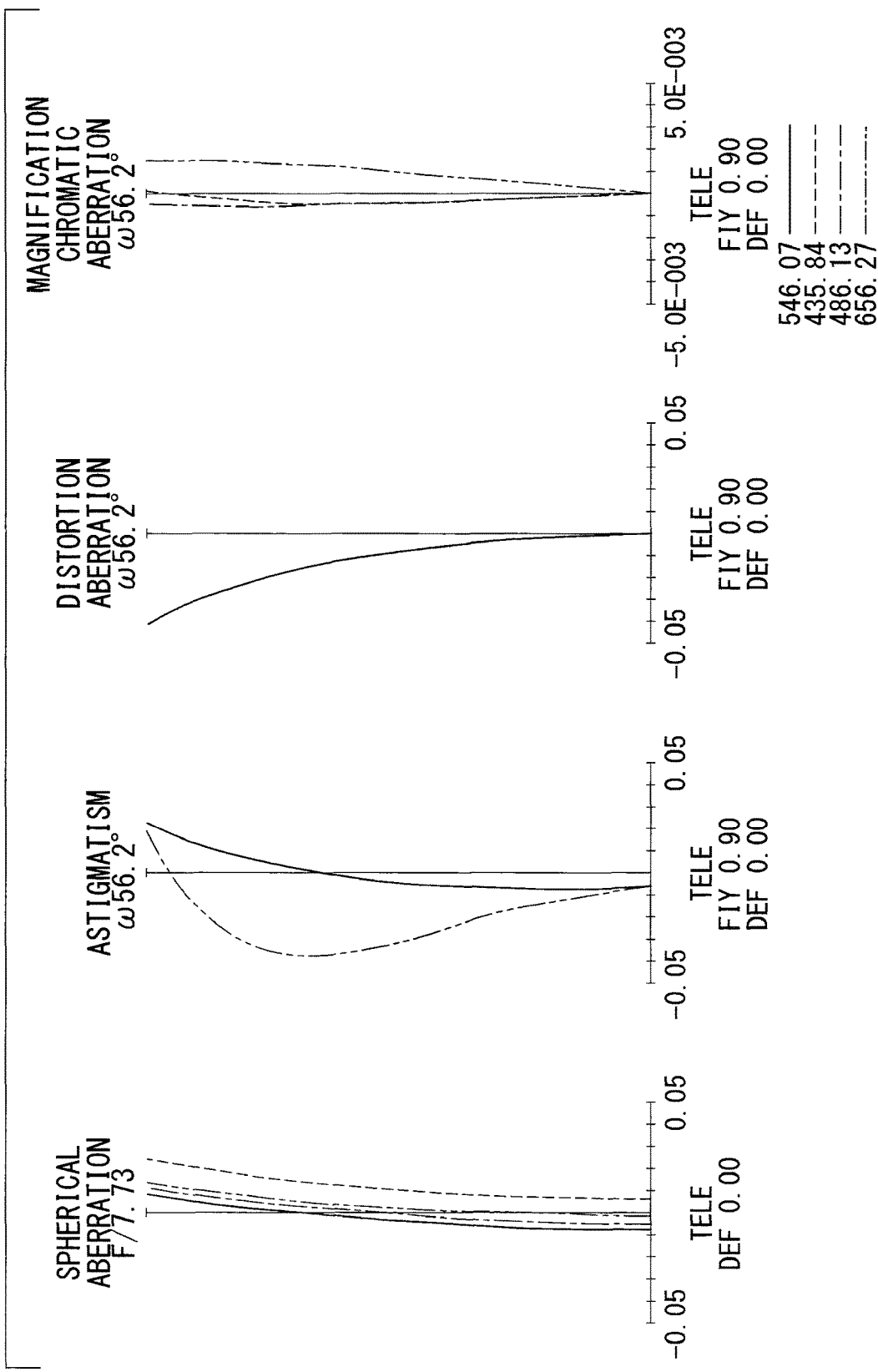
FIG. 13 is an aberration diagram of the middle state in the magnifying endoscope optical system according to the example 3 of the present invention.
Figure 14:
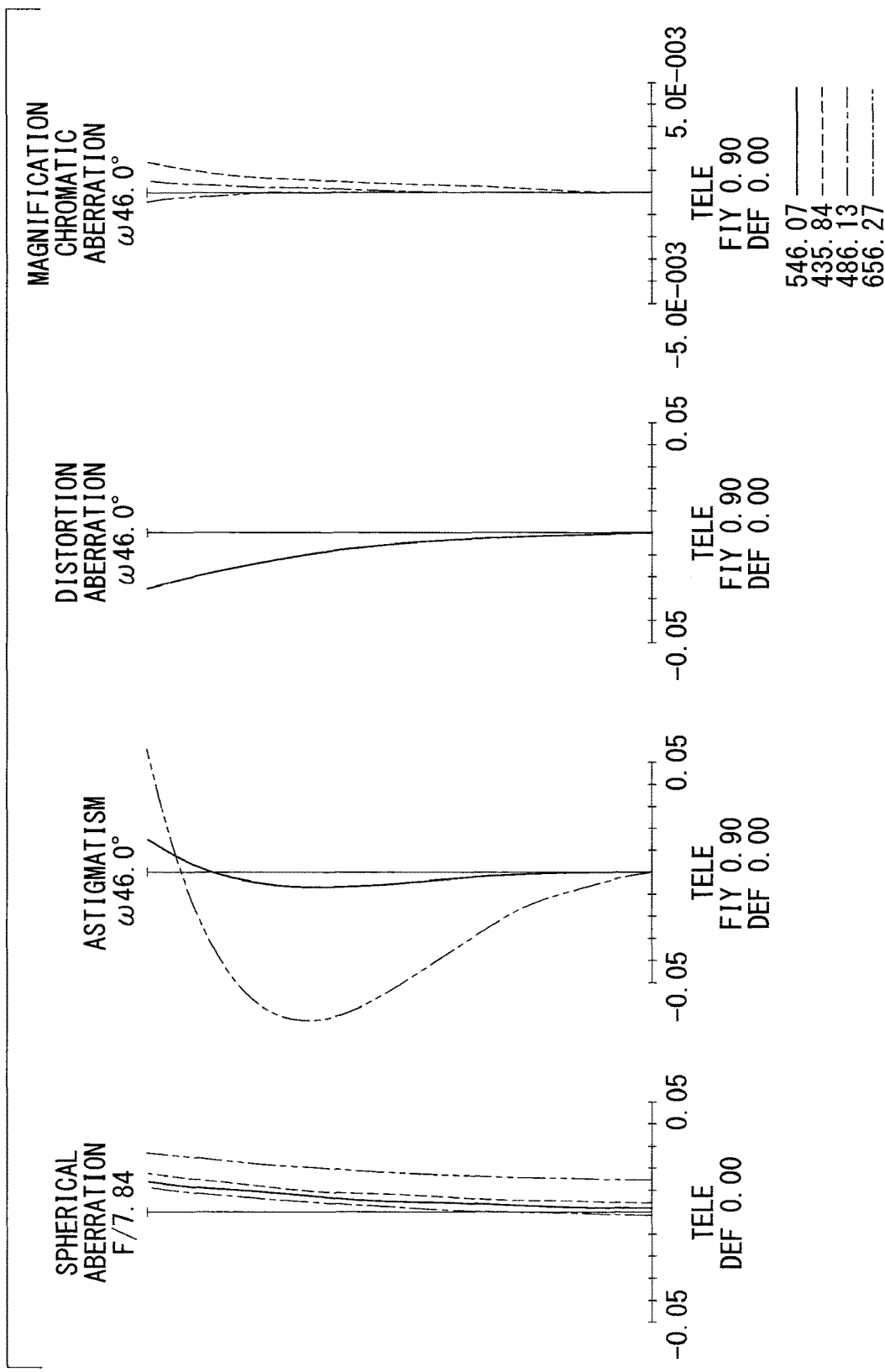
FIG. 14 is an aberration diagram of the proximity magnifying state (telescopic end) in the magnifying endoscope optical system according to the example 3 of the present invention.

Aberration diagrams of the magnifying endoscope optical system according to Example 3 are illustrated in FIGS. 12 to 14, respectively, and their lens data are shown below.

Lens Data

| Surface number | r | d | Ne | vd |
|---|---|---|---|---|
| 0 (Object surface) | ∞ | D0 | | |
| 1 | ∞ | 0.3454 | 1.88815 | 40.76 |
| 2 | 0.8054 | 0.6671 | | |
| 3 | ∞ | 0.5900 | 1.52300 | 65.13 |
| 4 | ∞ | 0.2568 | | |
| 5 | −3.7649 | 1.0563 | 1.59143 | 61.14 |

-continued

| Surface number | r | d | Ne | vd |
|---|---|---|---|---|
| 6 | −1.7320 | 0.0787 | | |
| 7 | 49.4159 | 1.0484 | 1.57392 | 52.95 |
| 8 | −1.8333 | 0.3156 | 1.93429 | 18.90 |
| 9 | −2.4621 | D1 | | |
| 10 (Diaphragm) | ∞ | 0.0300 | | |
| 11 | ∞ | 0.3071 | 1.88815 | 40.76 |
| 12 | 1.3418 | 0.5620 | 1.65222 | 33.79 |
| 13 | −14.6543 | D2 | | |
| 14 | 2.6500 | 0.8806 | 1.51825 | 64.14 |
| 15 | −4.7268 | 0.0786 | | |
| 16 | 4.2401 | 1.1769 | 1.53430 | 48.84 |
| 17 | −2.3186 | 0.4436 | 1.93429 | 18.90 |
| 18 | 23.1374 | 0.1283 | | |
| 19 | ∞ | 0.4000 | 1.52510 | 58.50 |
| 20 | ∞ | 0.6196 | | |
| 21 | −8.7307 | 0.6908 | 1.51825 | 64.14 |
| 22 | ∞ | 0.0099 | 1.51500 | 64.00 |
| 23 | ∞ | 0.6908 | 1.61350 | 50.49 |
| 24 | ∞ | | | |

Various Data

| | Normal observation state (wide angle end) | Middle state | Proximity magnifying state (telescopic end) |
|---|---|---|---|
| D0 | 10.3618 | 4.3000 | 2.0724 |
| D1 | 0.1974 | 0.8095 | 1.7763 |
| D2 | 1.8750 | 1.2629 | 0.2961 |
| fl | 1.004 | 1.057 | 1.1214 |
| Fno | 7.68 | 7.73 | 7.84 |

Example 4

Figure 15A:
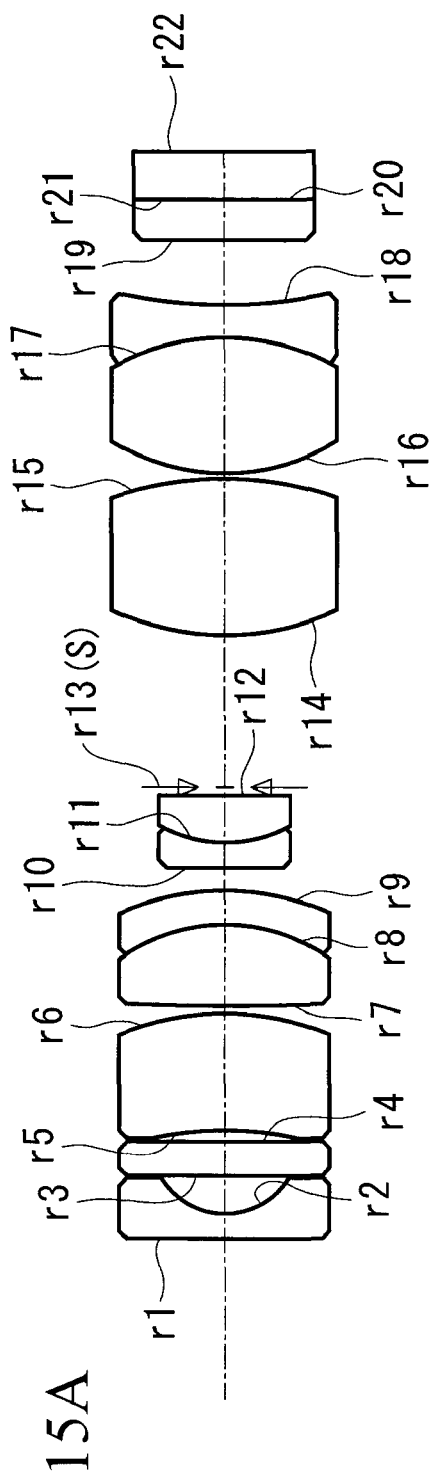
Figure 15B:
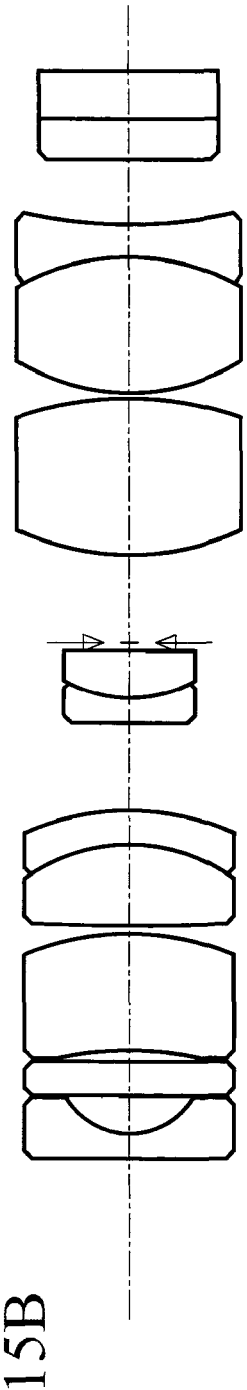
Figure 15C:
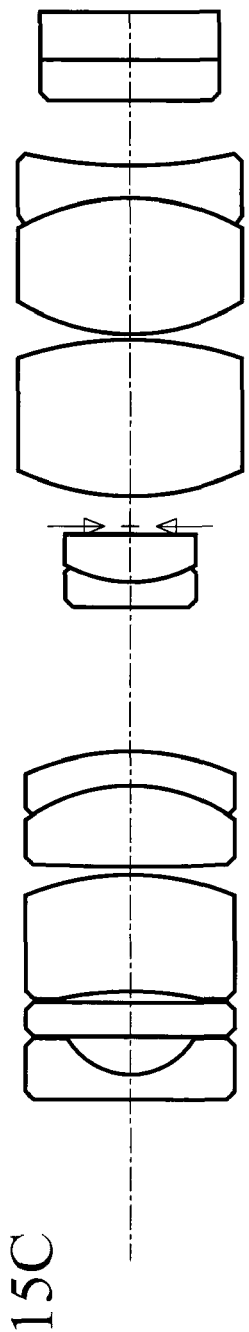

A sectional view showing the entire constitution of the magnifying endoscope optical system according to Example 4 of the present invention is illustrated in FIGS. 15A, 15B, and 15C.

The magnifying endoscope optical system according to Example 4 is constituted of the first lens group having a positive refractive power, the second lens group having a negative refractive power, the third lens group having a positive refractive power, and the fourth lens group having a negative refractive power in order from the object side. The diaphragm is arranged on the image side of the second lens group.

In Example 4, the second lens group moves integrally with the diaphragm on the optical axis to the image side and performs magnification from the normal observation state (wide angle end) to the proximity magnifying state (telescopic end) and focusing. That is, magnification and focusing are performed by moving the second lens group along the optical axis.

The first lens group is constituted of a plano-concave lens, a parallel planar plate, a positive meniscus lens with the convex surface directed to the image side, and a positive cemented lens in which a biconvex lens and a negative meniscus lens are cemented, the second lens group is constituted of a negative cemented lens in which a plano-concave lens and a positive meniscus lens with the convex surface directed to the object side are cemented, the third lens group is constituted of a biconvex lens and a positive cemented lens in which a biconvex lens and a biconcave lens are cemented, and the fourth lens group is constituted of a concave-plano lens. The diaphragm is arranged on the image side of the second lens group. The fourth lens group, the image pickup device sealing glass L1 and the image pickup surface are integrally bonded to each other.

In Example 4, by arranging the diaphragm on the image side end of the moving group, an effect of reducing the ray height of the third lens group is obtained, and it is advantageous when a lens diameter of the third lens group is to be made small in constituting lens driving components such as an actuator.

Example 4 satisfies the conditional expression (1) to the conditional expression (8) and as a result, the long stroke of the moving group and the large incident angle of the off-axis principal ray are ensured.

To the parallel planar plate, a filter for shutting off a specific wavelength such as a YAG laser at 1060 nm, a semiconductor laser at 810 nm or a light beam in a near-infrared region can be applied.

Figure 16:
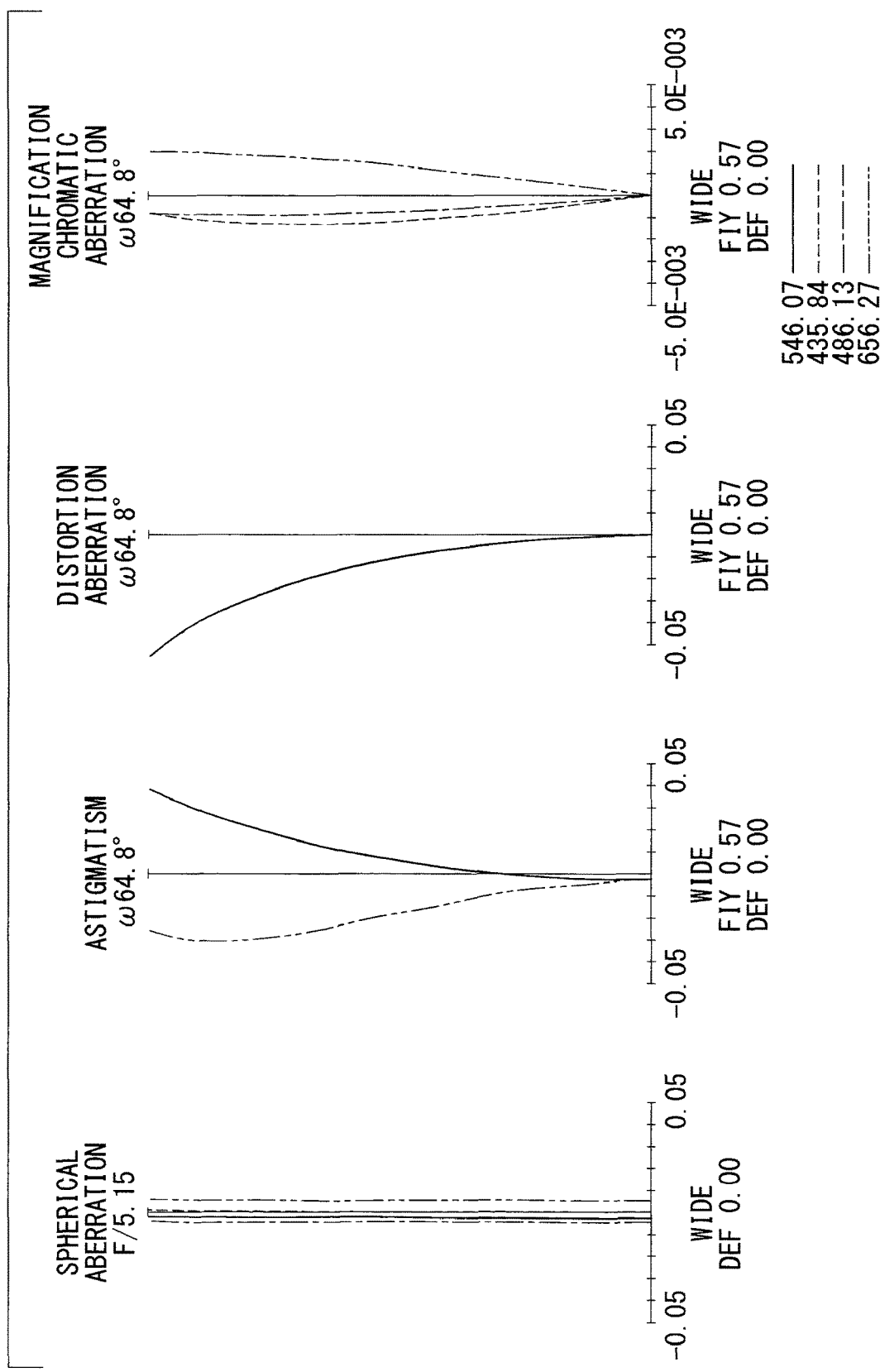
FIG. 16 is an aberration diagram of the normal observation state (wide angle end) in the magnifying endoscope optical system according to the example 4 of the present invention.
Figure 17:
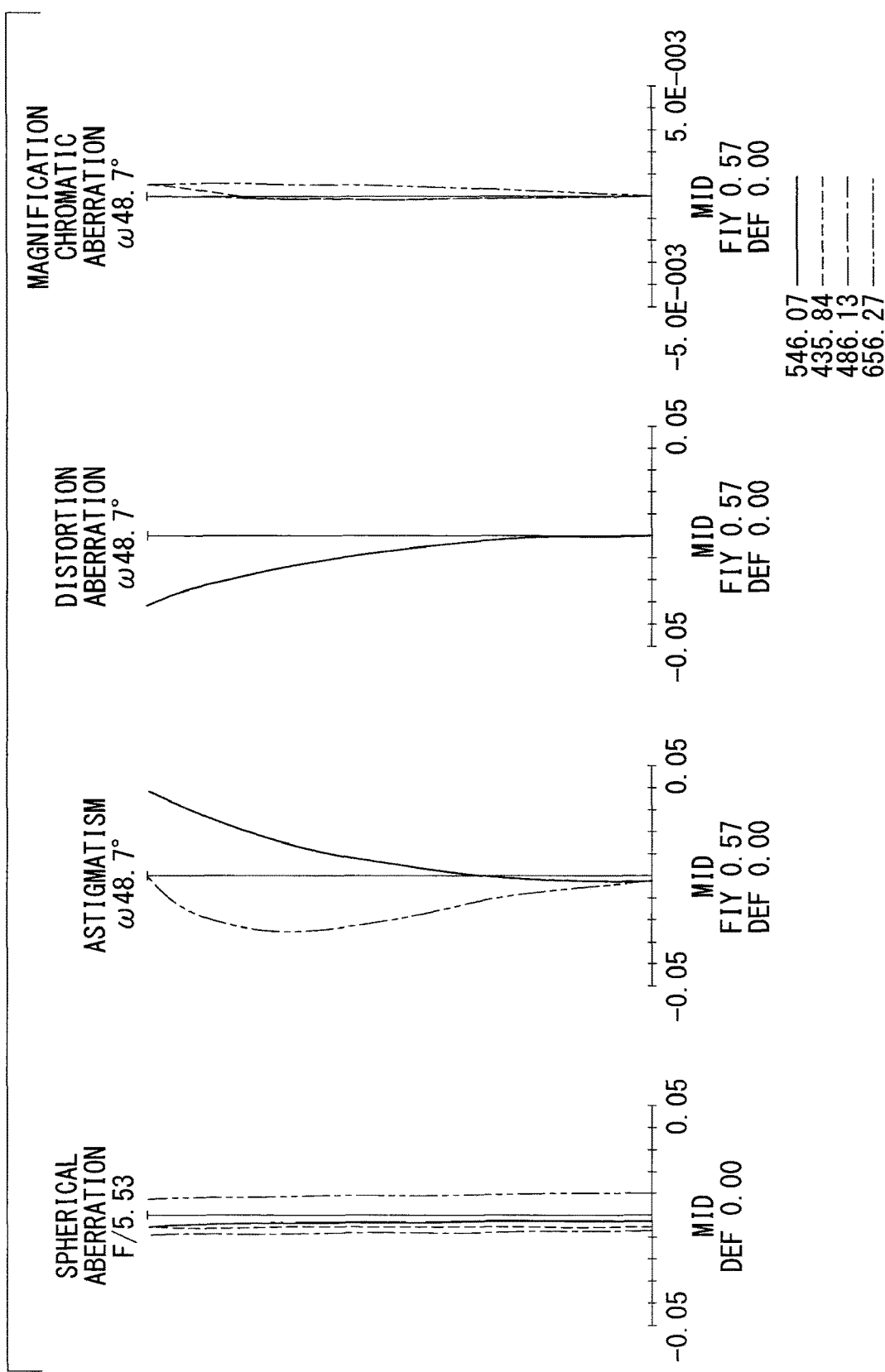
FIG. 17 is an aberration diagram of the middle state in the magnifying endoscope optical system according to the example 4 of the present invention.
Figure 18:
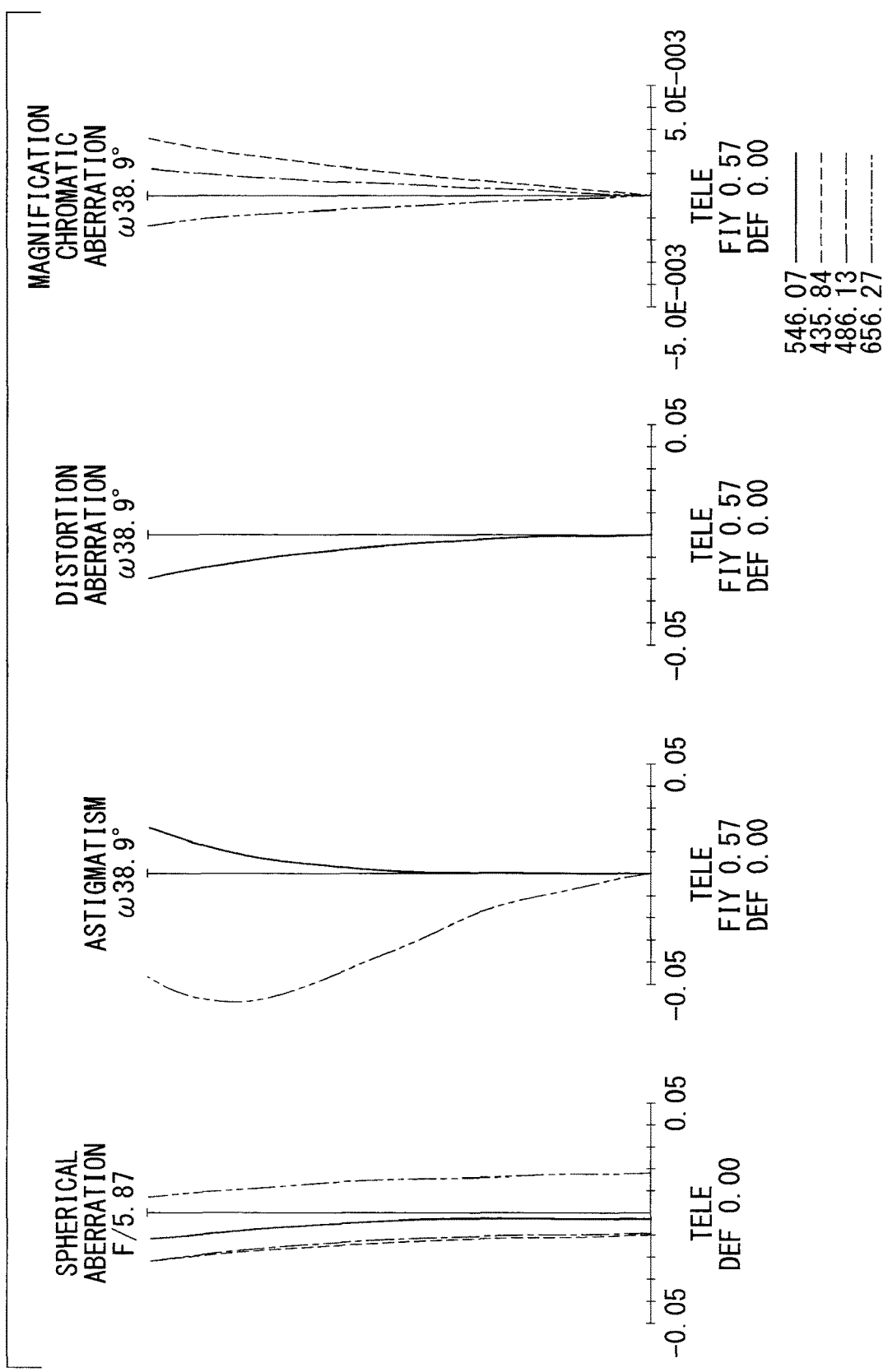
FIG. 18 is an aberration diagram of the proximity magnifying state (telescopic end) in the magnifying endoscope optical system according to the example 4 of the present invention.

Aberration diagrams of the magnifying endoscope optical system according to Example 4 are illustrated in FIGS. 16 to 18, respectively, and their lens data are shown below.

Lens Data

| Surface number | r | d | Ne | vd |
|---|---|---|---|---|
| 0 (Object surface) | ∞ | D0 | | |
| 1 | ∞ | 0.2200 | 1.88815 | 40.76 |
| 2 | 0.5910 | 0.3588 | | |
| 3 | ∞ | 0.3200 | 1.52300 | 65.13 |
| 4 | ∞ | 0.1300 | | |
| 5 | −1.8127 | 1.0384 | 1.88815 | 40.76 |
| 6 | −2.1662 | 0.0552 | | |
| 7 | 32.3983 | 0.7733 | 1.88815 | 40.76 |
| 8 | −1.2991 | 0.3093 | 1.93429 | 18.90 |
| 9 | −2.0889 | D1 | | |
| 10 | ∞ | 0.2209 | 1.88815 | 40.76 |
| 11 | 1.0792 | 0.4308 | 1.65222 | 33.79 |
| 12 | 7.6906 | 0.0331 | | |
| 13 (Diaphragm) | ∞ | D2 | | |
| 14 | 2.3275 | 1.4360 | 1.48915 | 70.23 |
| 15 | −3.1538 | 0.0552 | | |
| 16 | 1.7299 | 1.2703 | 1.58482 | 40.75 |
| 17 | −1.6592 | 0.2983 | 1.93429 | 18.90 |
| 18 | 3.5945 | 0.6019 | | |
| 19 | −11.0929 | 0.3645 | 1.51825 | 64.14 |
| 20 | ∞ | 0.0110 | 1.51500 | 64.00 |
| 21 | ∞ | 0.4419 | 1.50700 | 63.26 |
| 22 | ∞ | 0 | | |

Various Data

| | Normal observation state (wide angle end) | Middle state | Proximity magnifying state (telescopic end) |
|---|---|---|---|
| D0 | 11.0500 | 4.4186 | 2.5500 |
| D1 | 0.2209 | 0.7995 | 1.3256 |
| D2 | 1.4471 | 0.8686 | 0.3424 |
| fl | 0.6344 | 0.7426 | 0.8357 |
| Fno | 5.15 | 5.53 | 5.87 |

Example 5

Figure 19A:
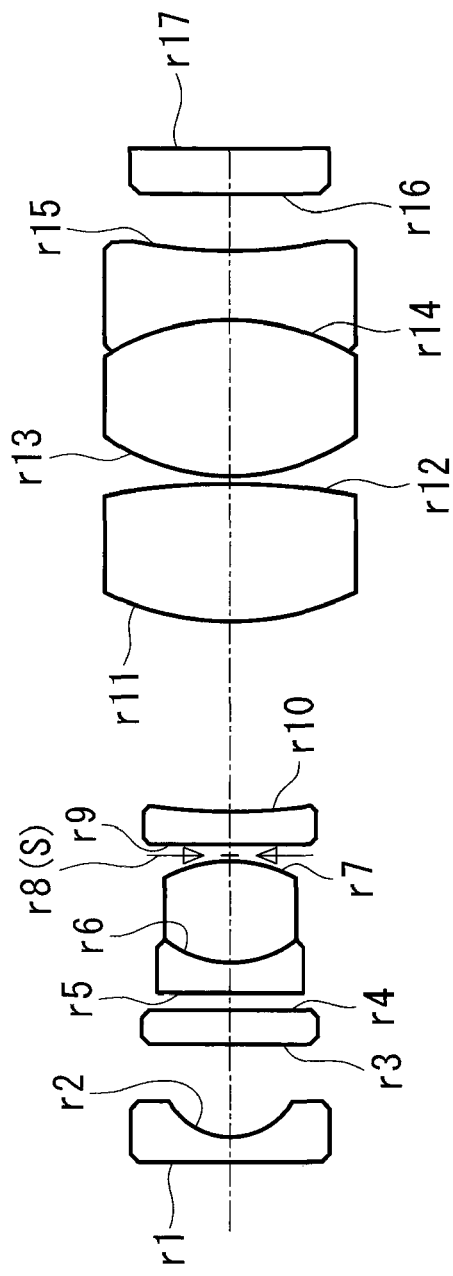
Figure 19B:
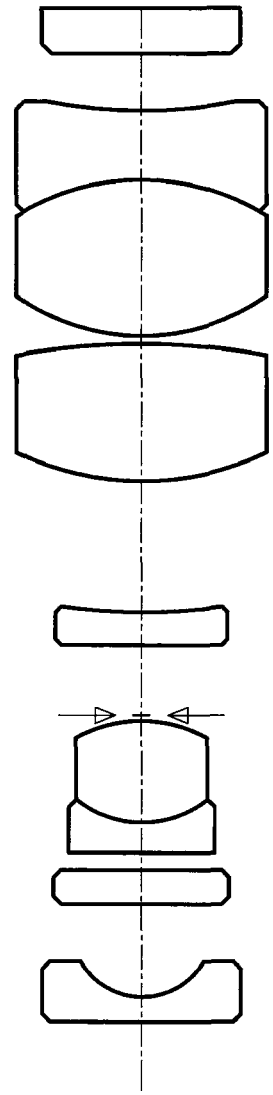
Figure 19C:
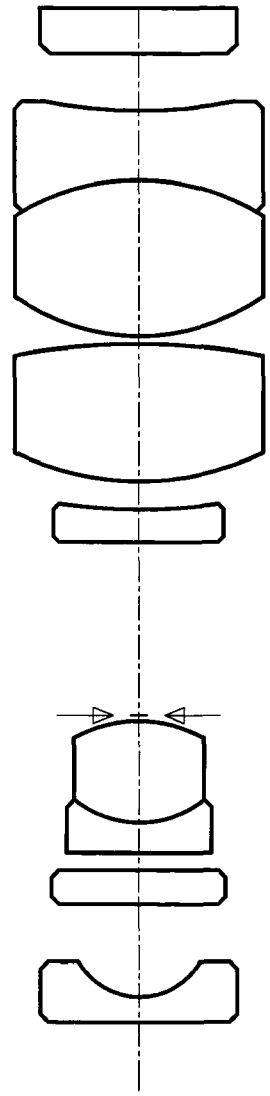

A sectional view showing the entire constitution of the magnifying endoscope optical system according to Example 5 of the present invention is illustrated in FIGS. 19A, 19B, and 19C.

The magnifying endoscope optical system according to Example 5 is constituted of the first lens group having a positive refractive power, the second lens group having a negative refractive power, the third lens group having a positive refractive power, and the fourth lens group having a negative refractive power in order from the object side. The diaphragm is arranged on the object side of the second lens group.

In the magnifying endoscope optical system according to Example 5, the second lens group moves on the optical axis to the image side and performs magnification from the normal observation state (wide angle end) to the proximity magnifying state (telescopic end) and focusing. That is, magnification and focusing are performed by moving the second lens group along the optical axis.

The first lens group is constituted of a plano-concave lens, a parallel planar plate, a positive cemented lens in which a negative meniscus lens with the convex surface directed to the object side and a biconvex lens are cemented, the second lens group is constituted of a plano-concave lens, the third lens group is constituted of a biconvex lens and a positive cemented lens in which a biconvex lens and a biconcave lens are cemented, and the fourth lens group is constituted of a concave-plano lens. The concave-plano lens of the fourth lens group and the image pickup surface are integrally bonded to each other.

Example 5 satisfies the conditional expression (1) to the conditional expression (8) and as a result, the long stroke of the moving group and the large incident angle of the off-axis principal ray are ensured.

To the parallel planar plate, a filter for shutting off a specific wavelength such as a YAG laser at 1060 nm, a semiconductor laser at 810 nm or a light beam in a near-infrared region can be applied.

Figure 20:
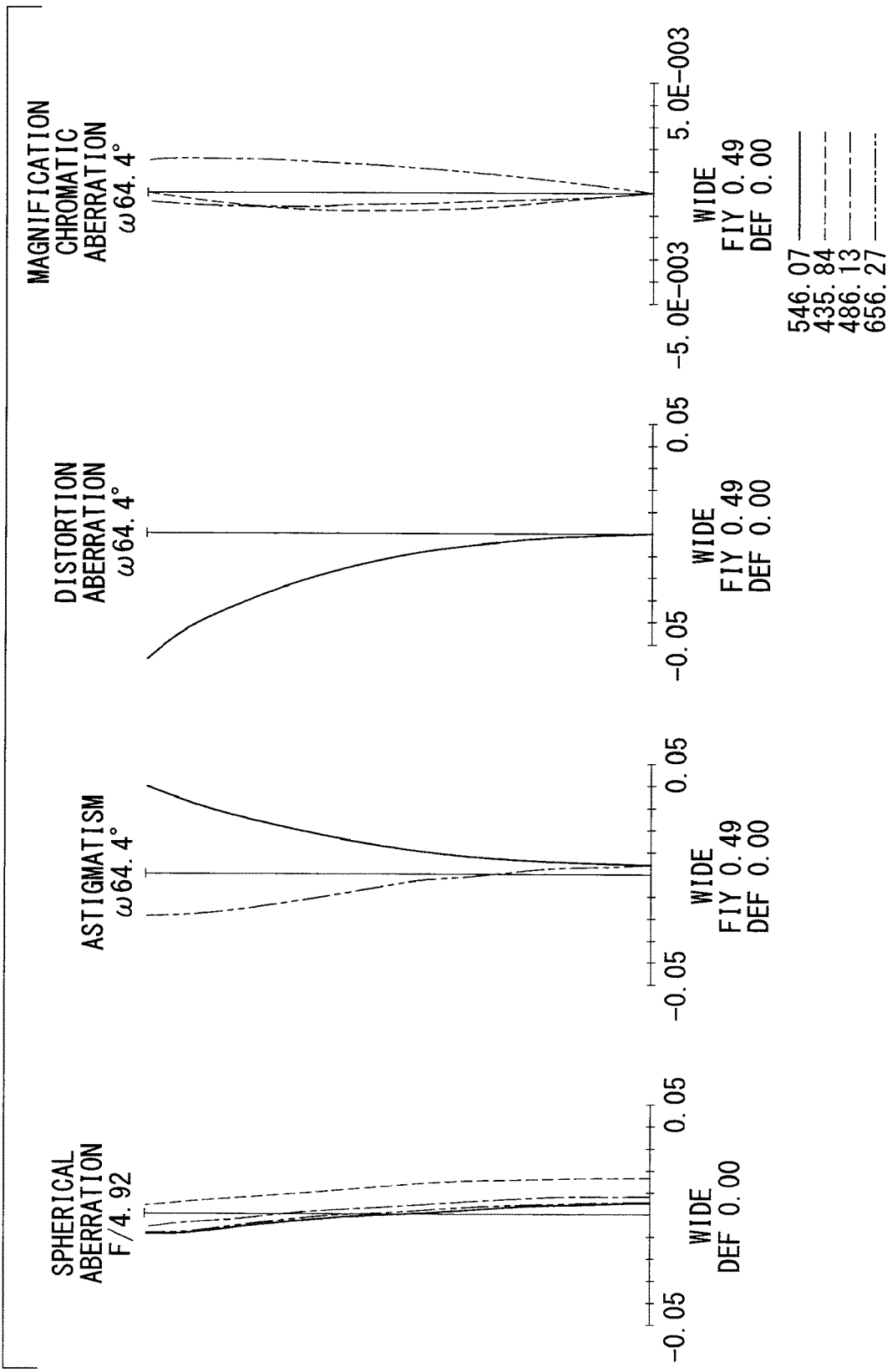
FIG. 20 is an aberration diagram of the normal observation state (wide angle end) in the magnifying endoscope optical system according to the example 5 of the present invention.
Figure 21:
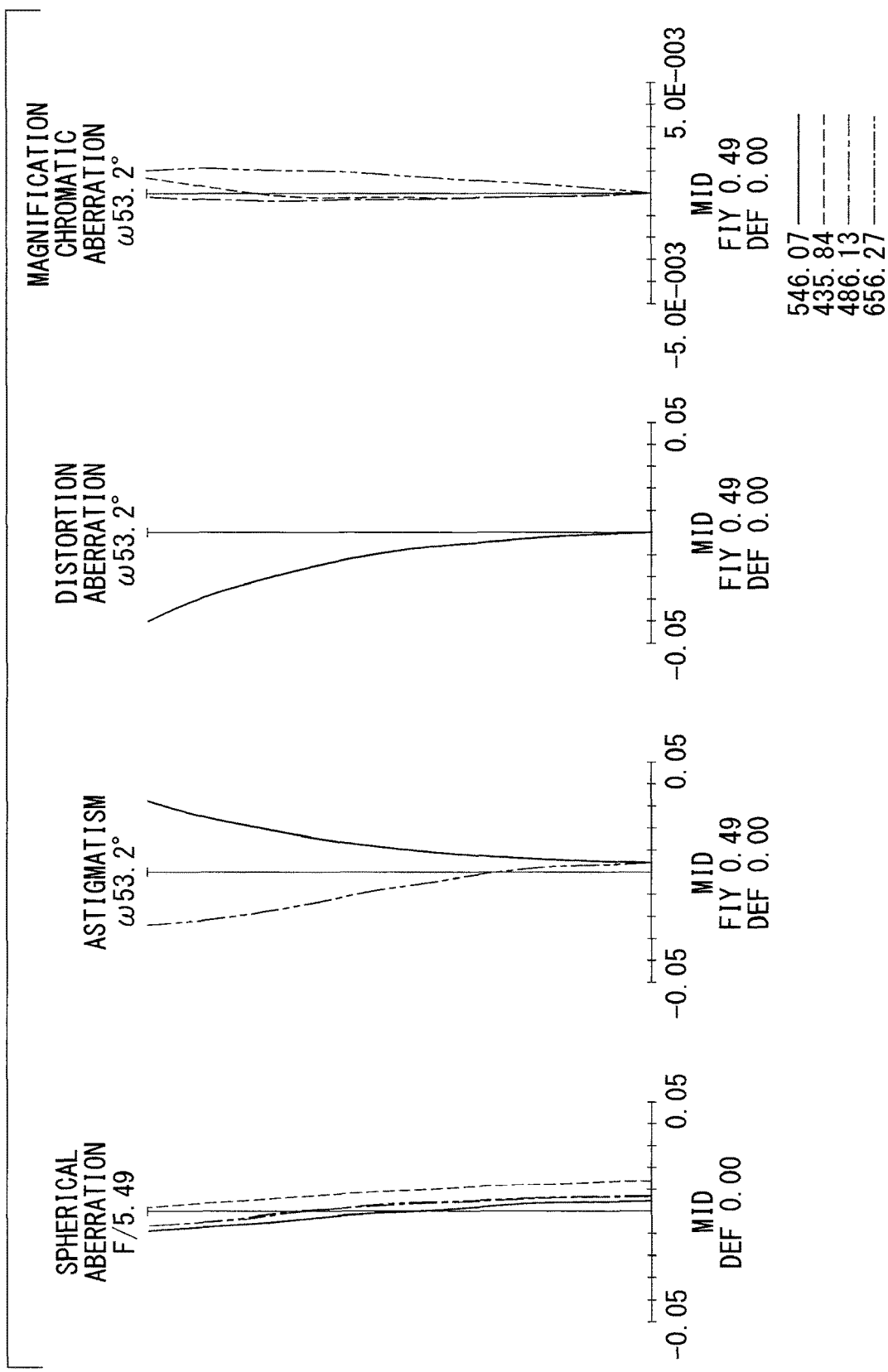
FIG. 21 is an aberration diagram of the middle state in the magnifying endoscope optical system according to the example 5 of the present invention.
Figure 22:
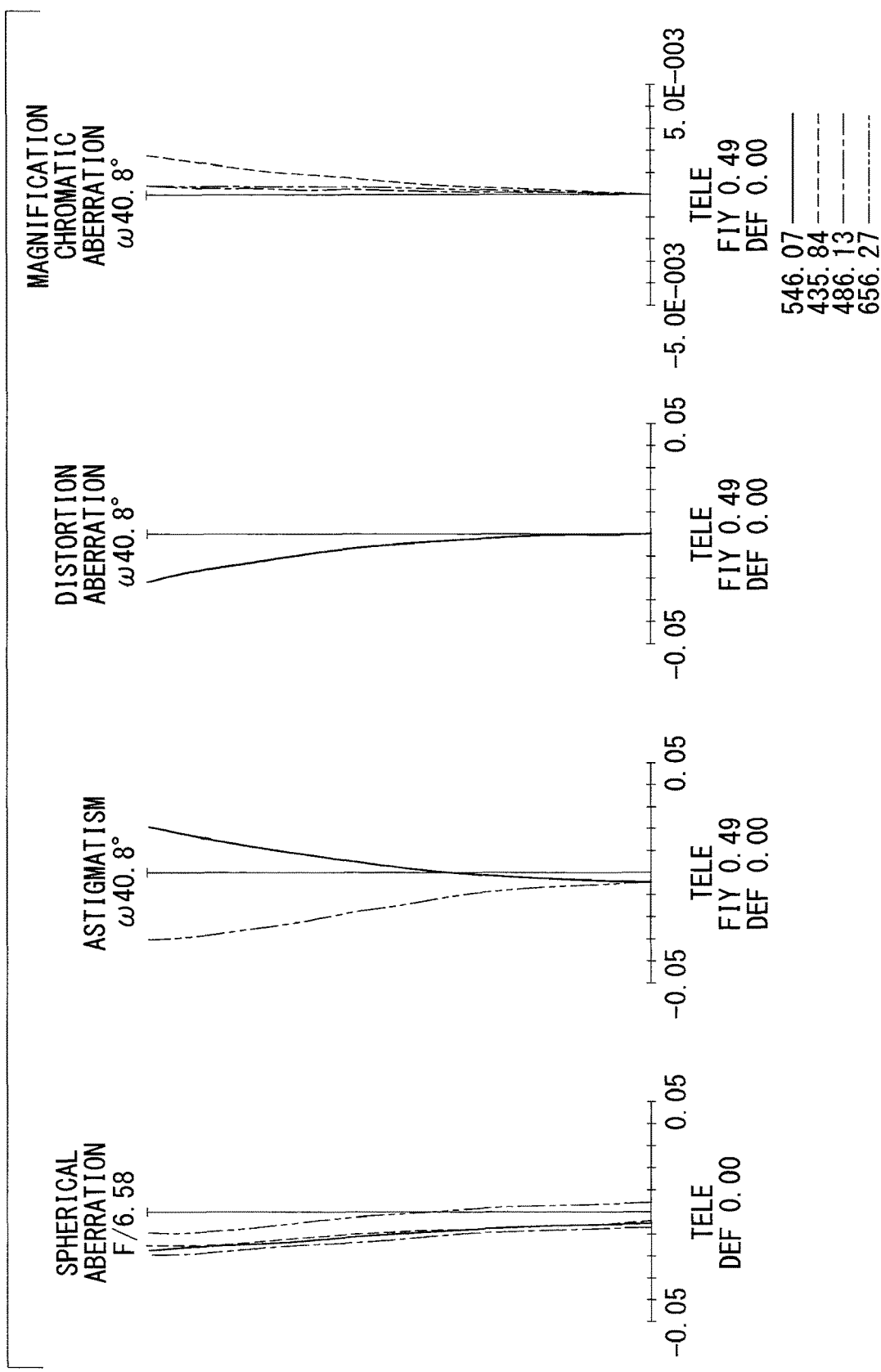
FIG. 22 is an aberration diagram of the proximity magnifying state (telescopic end) in the magnifying endoscope optical system according to the example 5 of the present invention.

Aberration diagrams of the magnifying endoscope optical system according to Example 5 are illustrated in FIGS. 20 to 22, respectively, and their lens data are shown below.

Lens Data

| Surface number | r | d | Ne | vd |
|---|---|---|---|---|
| 0 (Object surface) | ∞ | D0 | | |
| 1 | ∞ | 0.1900 | 1.88814 | 40.78 |
| 2 | 0.4843 | 0.7174 | | |
| 3 | ∞ | 0.2700 | 1.52300 | 65.13 |
| 4 | ∞ | 0.1234 | | |
| 5 | 13.0714 | 0.2374 | 1.88815 | 40.76 |
| 6 | 0.6923 | 0.7787 | 1.73234 | 54.68 |
| 7 | −1.0180 | 0.0475 | 1. | |
| 8 (Diaphragm) | ∞ | D1 | | |
| 9 | ∞ | 0.2350 | 1.73234 | 54.68 |
| 10 | 2.9163 | D2 | | |
| 11 | 1.8992 | 1.0731 | 1.48915 | 70.23 |
| 12 | −4.2752 | 0.0475 | | |
| 13 | 1.4102 | 1.2155 | 1.48915 | 70.23 |
| 14 | −1.5583 | 0.5413 | 1.93429 | 18.90 |
| 15 | 3.6123 | 0.4629 | | |
| 16 | −18.2212 | 0.3324 | 1.51825 | 64.14 |
| 17 | ∞ | 0. | | |

Various Data

| | Normal observation state (wide angle end) | Middle state | Proximity magnifying state (telescopic end) |
|---|---|---|---|
| D0 | 9.4961 | 4.50 | 2.28 |
| D1 | 0.0950 | 0.5378 | 1.3295 |
| D2 | 1.4719 | 1.0290 | 0.2374 |
| fl | 0.566 | 0.622 | 0.7109 |
| Fno | 4.92 | 5.49 | 6.58 |

Example 6

Figure 23A:
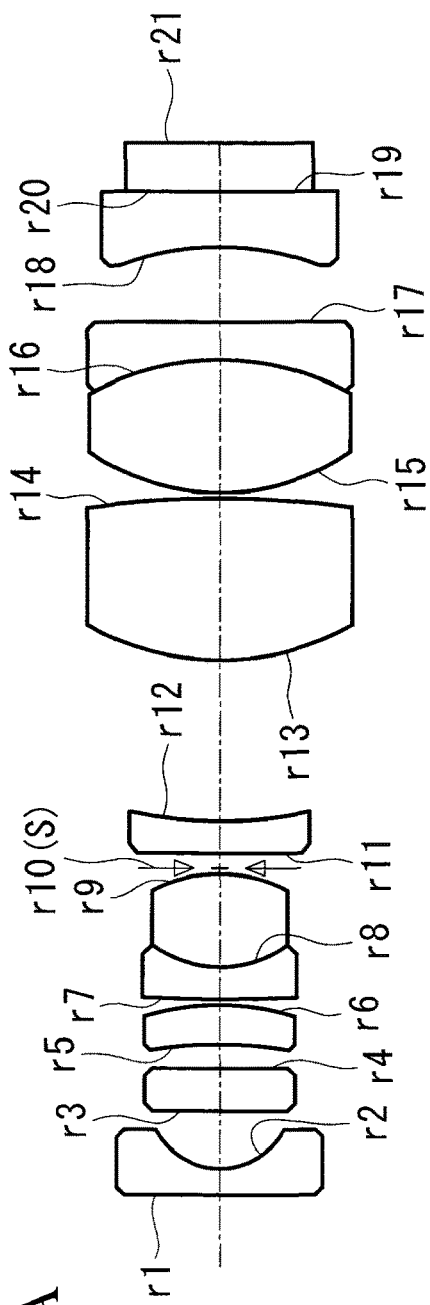
Figure 23B:
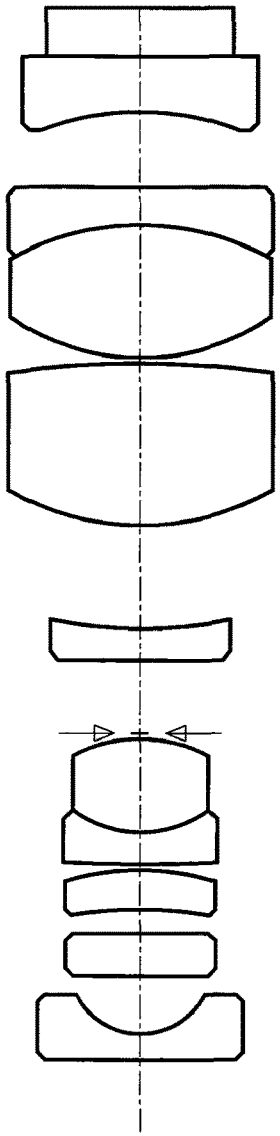
Figure 23C:
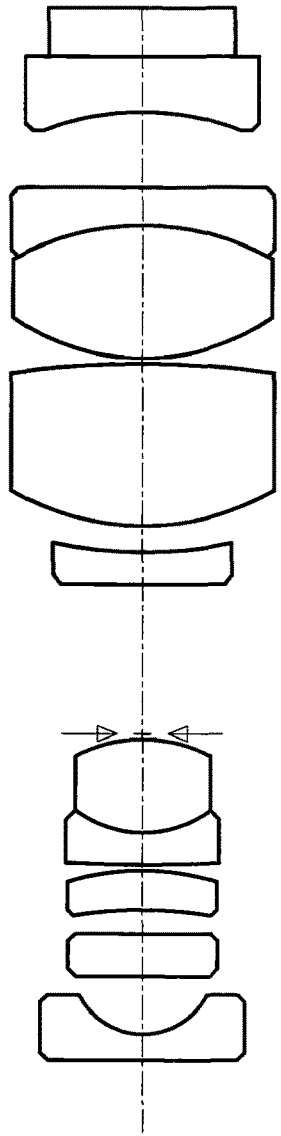

A sectional view showing the entire constitution of the magnifying endoscope optical system according to Example 6 of the present invention is illustrated in FIGS. 23A, 23B, and 23C.

The magnifying endoscope optical system according to Example 6 is constituted of the first lens group having a positive refractive power, the second lens group having a negative refractive power, the third lens group having a positive refractive power, and the fourth lens group having a negative refractive power in order from the object side. The diaphragm is arranged on the object side of the second lens group.

In the magnifying endoscope optical system according to Example 6, the second lens group moves on the optical axis to the image side and performs magnification from the normal observation state (wide angle end) to the proximity magnifying state (telescopic end) and focusing. That is, magnification and focusing are performed by moving the second lens group along the optical axis.

The first lens group is constituted of a plano-concave lens, a parallel planar plate, a positive meniscus lens with the convex surface directed to the image side, and a positive cemented lens in which a negative meniscus lens with the convex surface directed to the object side and a biconvex lens are cemented, the second lens group is constituted of a plano-concave lens, the third lens group is constituted of a biconvex lens and a positive cemented lens in which a biconvex lens and a biconcave lens are cemented, and the fourth lens group is constituted of a concave-plano lens. The concave-plano lens of the fourth lens group, the image pickup device sealing glass, and the image pickup surface are integrally bonded to each other.

Example 6 satisfies the conditional expression (1) to the conditional expression (8) and as a result, the long stroke of the moving group and the large incident angle of the off-axis principal ray are ensured.

To the parallel planar plate, a filter for shutting off a specific wavelength such as a YAG laser at 1060 nm, a semiconductor laser at 810 nm or a light beam in a near-infrared region can be applied.

Figure 24:
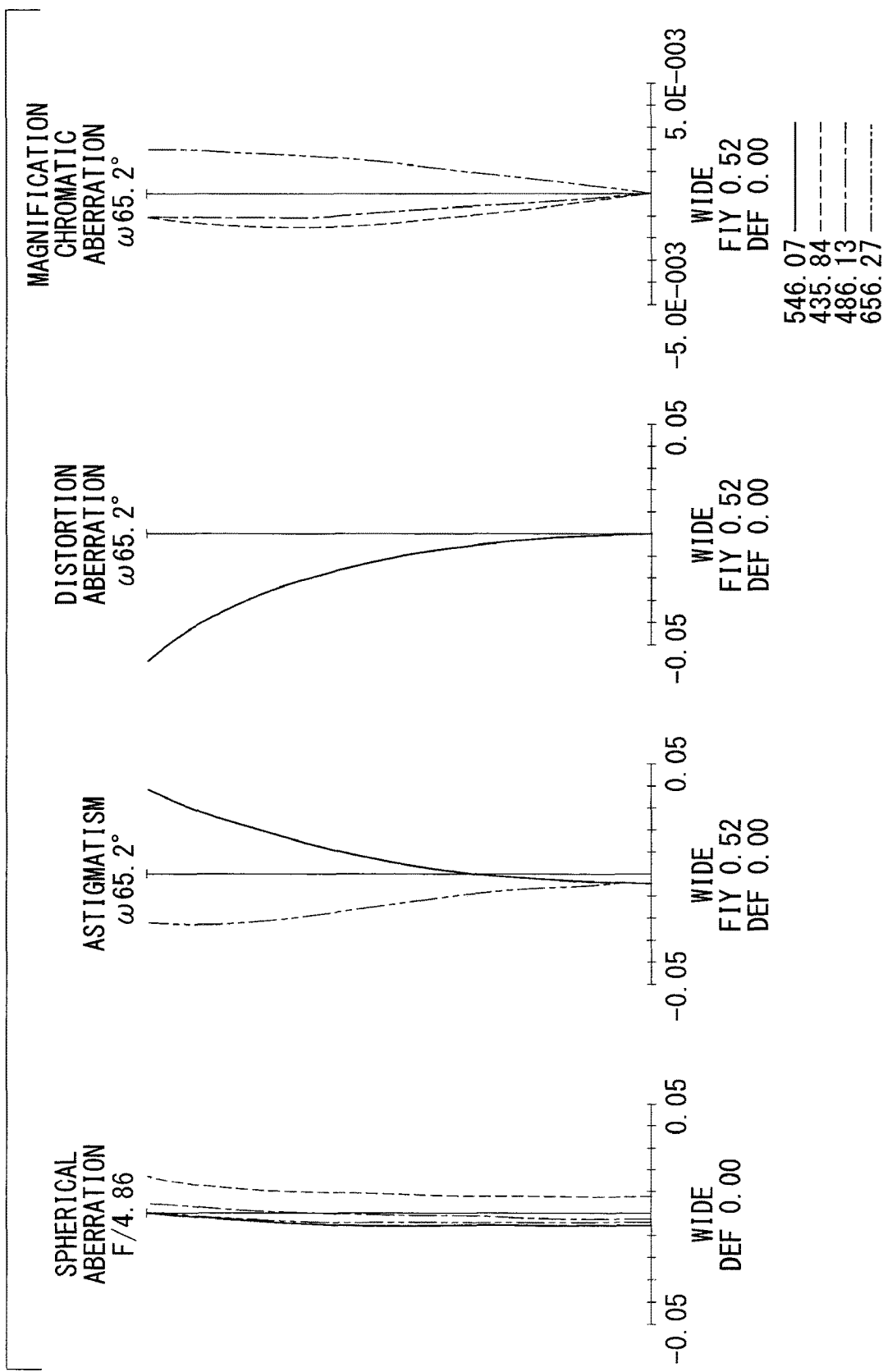
FIG. 24 is an aberration diagram of the normal observation state (wide angle end) in the magnifying endoscope optical system according to the example 6 of the present invention.
Figure 25:
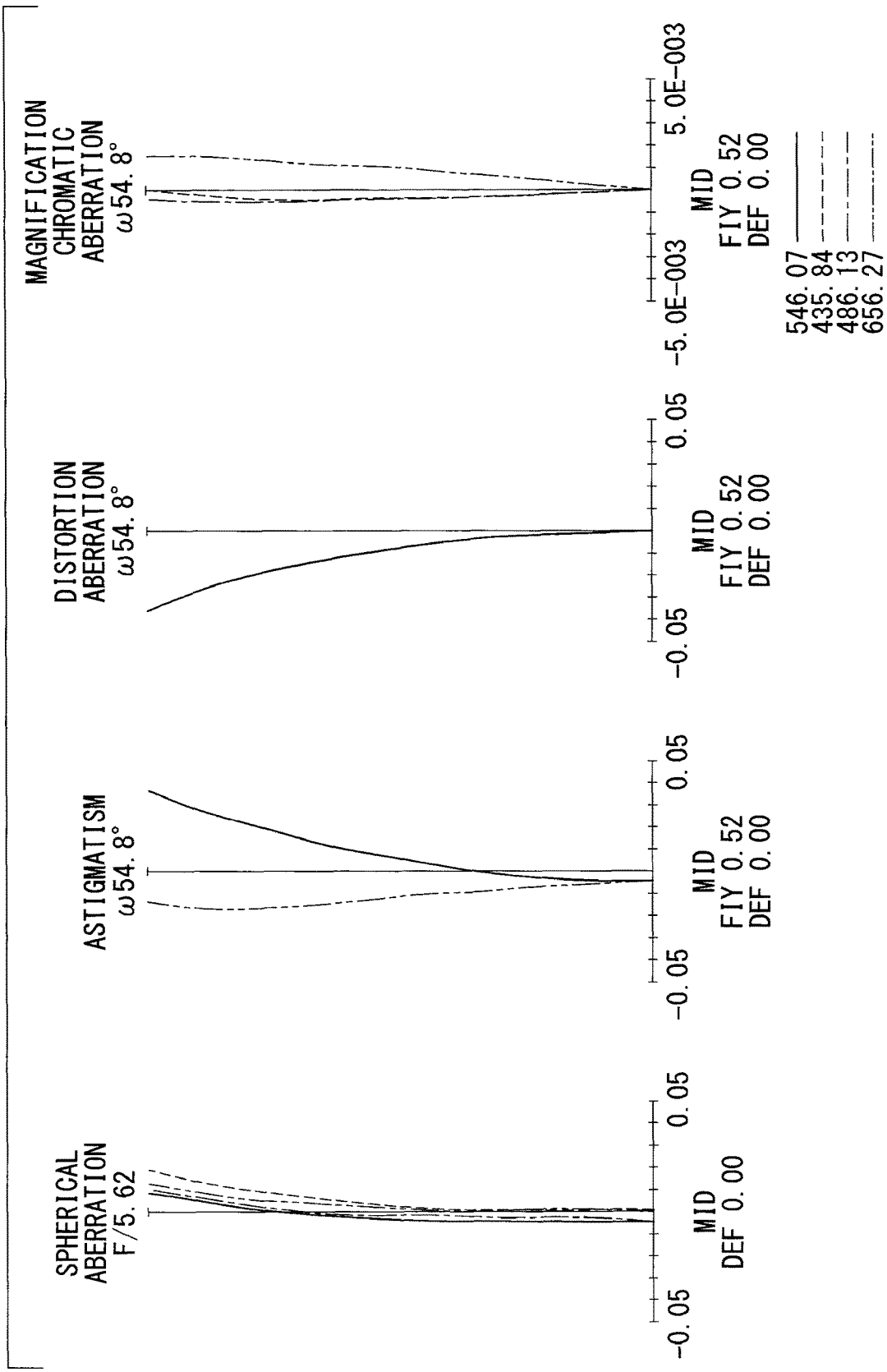
FIG. 25 is an aberration diagram of the middle state in the magnifying endoscope optical system according to the example 6 of the present invention.
Figure 26:
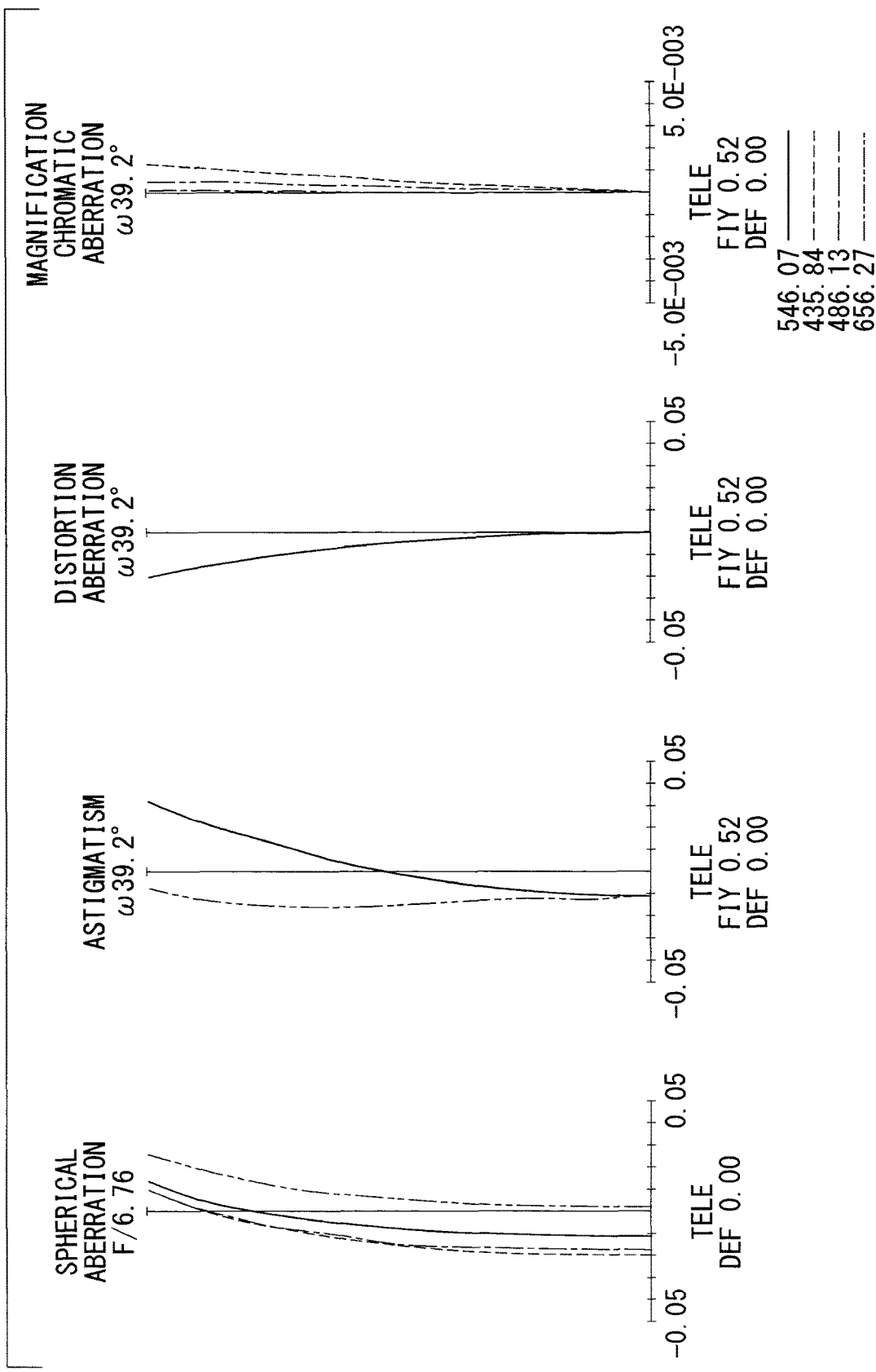
FIG. 26 is an aberration diagram of the proximity magnifying state (telescopic end) in the magnifying endoscope optical system according to the example 6 of the present invention.

Aberration diagrams of the magnifying endoscope optical system according to Example 6 are illustrated in FIGS. 24 to 26, respectively, and their lens data are shown below.

Lens Data

| Surface number | r | d | Ne | vd |
|---|---|---|---|---|
| 0 (Object surface) | ∞ | D0 | | |
| 1 | ∞ | 0.2000 | 1.88814 | 40.78 |
| 2 | 0.4969 | 0.4584* | | |
| 3 | ∞ | 0.3500 | 1.52300 | 65.13 |
| 4 | ∞ | 0.2016 | | |
| 5 | −1.5468 | 0.3015 | 1.51977 | 52.43 |
| 6 | −1.2434 | 0.0532 | | |
| 7 | 13.1293 | 0.2443 | 1.88815 | 40.76 |
| 8 | 0.7355 | 0.7496 | 1.72341 | 50.23 |
| 9 | −1.1468 | 0.0504 | | |
| 10 (Diaphragm) | ∞ | D1 | | |
| 11 | ∞ | 0.2519 | 1.82017 | 46.62 |
| 12 | 2.5488 | D2 | | |
| 13 | 1.8930 | 1.2981 | 1.48915 | 70.23 |
| 14 | −6.4504 | 0.0502 | | |
| 15 | 1.6370 | 1.0600 | 1.59143 | 61.14 |
| 16 | −1.8353 | 0.3195 | 1.93429 | 18.90 |
| 17 | ∞ | 0.5887 | | |
| 18 | −1.7300 | 0.4535 | 1.51825 | 64.14 |
| 19 | ∞ | 0.0150 | 1.51500 | 64.00 |

-continued

| Surface number | r | d | Ne | vd |
|---|---|---|---|---|
| 20 | ∞ | 0.3900 | 1.50700 | 63.26 |
| 21 | ∞ | | | |

Various Data

| | Normal observation state (wide angle end) | Middle state | Proximity magnifying state (telescopic end) |
|---|---|---|---|
| D0 | 10.0775 | 4.5000 | 2.3500 |
| D1 | 0.1209 | 0.5826 | 1.1992 |
| D2 | 1.3000 | 0.8384 | 0.2217 |
| fl | 0.589 | 0.669 | 0.764 |
| Fno | 4.86 | 5.62 | 6.76 |

In the aforementioned Example 1 to Example 6, values according to the aforementioned expressions (1) to (8) are shown in Table 1.
{Table 1}

TABLE 1

| | EXAMPLE 1 | EXAMPLE 2 | EXAMPLE 3 | EXAMPLE 4 | EXAMPLE 5 | EXAMPLE 6 |
|---|---|---|---|---|---|---|
| CONDITIONAL EXPRESSION(1) $-65 < fr/fw < -2$ | −8.90 | −13.26 | −16.78 | −33.76 | −62.12 | −5.67 |
| CONDITIONAL EXPRESSION(2) $-60 < Rr/R01 < -2$ | −5.27 | −8.00 | −10.84 | −18.77 | −37.62 | −3.48 |
| CONDITIONAL EXPRESSION(3) $0.15 < Tr/fw < 1.7$ | 0.56 | 0.56 | 0.69 | 0.57 | 0.59 | 0.77 |
| CONDITIONAL EXPRESSION(4) $5 < fr/f01 < 68$ | 9.02 | 13.71 | 18.57 | 32.19 | 64.51 | 5.97 |
| CONDITIONAL EXPRESSION(5) $1.2 < dm/fw < 2.4$ | 1.83 | 1.94 | 1.57 | 1.74 | 2.18 | 1.83 |
| CONDITIONAL EXPRESSION(6) $0.9 < f4/f2 < 9.5$ | 1.44 | 2.01 | 2.17 | 6.60 | 8.83 | 1.07 |
| CONDITIONAL EXPRESSION(7) $-0.6 < expi(w)/\Sigma d < -0.3$ | −0.53 | −0.43 | −0.51 | −0.43 | −0.51 | −0.49 |
| CONDITIONAL EXPRESSIONAL(8) $-25 < f4/f1 < -2$ | −3.51 | −5.19 | −7.63 | −14.61 | −22.28 | −2.46 |

According to this aspect, aberrations are favorably corrected, while a long stroke of a moving group and a large incident angle of the off-axis principal ray are ensured at the same time, and excellent operability and endoscopic observation with a high-quality image can be realized. That is, by satisfying the conditional expression (1), even if the stroke of the moving group is ensured to be long, the large incident angle of the off-axis principal ray can be ensured by an effect of exit pupil positional adjustment of the negative lens cemented to the image pickup device, and off-axis aberration such as field curvature and astigmatism which are problems in a magnification optical system can be favorably corrected.

In the aforementioned aspect, a negative first lens is provided on a side closest to an object, and the following conditional expression (2) is preferably satisfied:

$$-60 < Rr/R01 < -2 \quad (2)$$

where reference character Rr denotes a radius of curvature of a surface of the negative single lens cemented to the image pickup device on the object side, and reference character R01 denotes a radius of curvature of a surface of the negative first lens on an image side.

The conditional expression (2) regulates refractive powers of the negative first lens and the negative lens cemented to the image pickup device. By satisfying the conditional expression (2), the radius of curvature of the surface of the negative lens cemented to the image pickup device on the object side and the radius of curvature of the surface of the negative first lens on the image side are kept appropriately, while setting of the exit pupil position is made appropriately and the large incident angle of the off-axis principal ray is ensured, and aberration correction can be performed favorably.

In the aforementioned aspect, the following conditional expression (3) is favorably satisfied:

$$0.15 < Tr/fw < 1.7 \quad (3)$$

where reference character Tr denotes a middle thickness of the negative single lens cemented to the image pickup device.

The conditional expression (3) regulates the middle thickness of the negative lens cemented to the image pickup device and a focal distance of the normal observation state (wide angle end). By satisfying the conditional expression (3), the middle thickness of the negative lens cemented to the image pickup device is made appropriate, the exit pupil positional adjustment can be performed appropriately, and strength of the lens can be kept appropriately. Moreover, the entire length of the objective optical system is not too long, which is advantageous for size reduction.

In the aforementioned aspect, the negative first lens is provided on a side closest to an object, and the following conditional expression (4) is preferably satisfied:

$$5 < fr/f01 < 68 \quad (4)$$

where, reference character f01 denotes a focal distance of the negative first lens.

The conditional expression (4) regulates the refractive powers of the first lens and the negative lens cemented to the image pickup device. By satisfying the conditional expression (4), the refractive power of the negative lens is made an appropriate value, and both the exit pupil positional adjustment and aberration correction can be performed favorably.

In the aforementioned aspect, it is preferable that a positive first group, a negative second group, a positive third group, and a negative fourth group be provided in order from the object side, the fourth group have a negative single lens cemented to the image pickup device, the negative single lens be a negative single lens with a concave surface directed to the object side, an image position be adjusted within the group interval between the third group and the fourth group, and focusing and magnification be made by moving only the second group on the optical axis.

By constituting as above, the refractive power of the moving lens group can be made a proper value, and the stroke can be ensured to be long, and moreover, a change in observation power with respect to a moving amount of the moving lens group (hereinafter referred to as magnification sensitivity) can be made small, and magnification can be made gently. That is, the focusing operation in magnification can be facilitated, and excellent operability can be provided to an operator.

In the aforementioned aspect, the following conditional expressions (5) to (7) are preferably satisfied:

$$1.2 < dm/fw < 2.4 \quad (5)$$

$$0.9 < f4/f2 < 9.5 \quad (6)$$

$$-0.6 < \text{expi}(w)/\Sigma d < -0.3 \quad (7)$$

where reference character dm denotes a moving amount of the second group, reference character f4 denotes a focal distance of the fourth group, reference character f2 denotes a focal distance of the second group, reference character expi(w) denotes an exit pupil position of a maximum image height actual ray in the normal observation state (wide angle end), and reference character $\Sigma d$ denotes the entire length of the optical system.

The conditional expression (5) regulates a stroke of the moving lens group. By satisfying the conditional expression (5), the stroke of the moving group is made an appropriate length, and while the large incident angle of the off-axis principal ray is ensured, the magnification sensitivity is made an appropriate value, and the operability can be improved.

The conditional expression (6) regulates refractive powers of the second group and the fourth group. By satisfying the conditional expression (6), while the long stroke of the second group which is the moving group is ensured, the large incident angle of the off-axis principal ray can be ensured.

The conditional expression (7) regulates exit pupil arrangement. By satisfying the conditional expression (7), while the large incident angle of the off-axis principal ray is ensured, aberration correction can be performed favorably.

In the aforementioned aspect, the following conditional expression (8) is preferably satisfied:

$$-25 < f4/f1 < -2 \quad (8)$$

where reference character f1 denotes the focal distance of the first group.

The conditional expression (8) regulates refractive powers of the fourth group and the first group. By satisfying the conditional expression (8), while aberration correction is favorably performed, the large incident angle of the off-axis principal ray can be ensured.

Advantageous Effects of Invention

According to the present invention, the stroke of the moving lens group is kept long, the large incident angle of the off-axis principal ray is ensured, and an effect of size reduction while the focusing operation in magnification is easy can be exerted.

REFERENCE SIGNS LIST

G1 first lens group
G2 second lens group
G3 third lens group
G4 fourth lens group
L1 first lens
L2 second lens
L3 third lens
L4 fourth lens
L5 fifth lens
L6 sixth lens
L7 seventh lens
L8 eighth lens
L9 ninth lens
L10 tenth lens
CL1 cemented lens
CL2 cemented lens

The invention claimed is:

1. A magnifying endoscope optical system comprising:
a negative single lens cemented to an image pickup device, a moving lens group, and a first group having a negative first lens that is provided on a side closer to an object than the moving lens group, wherein
the negative first lens is provided on a side closest to the object;
switching at least between a normal observation state and a proximity magnifying state can be made by moving the moving lens group; and
the following conditional expressions (1) and (2) are satisfied:

$$-65 < fr/fw < -2 \quad (1)$$

$$-60 < Rr/R01 < -2 \quad (2)$$

where reference character fr denotes a focal distance of the negative lens cemented to the image pickup device, reference character fw denotes a focal distance of the entire system in the normal observation state, and reference character Rr denotes a radius of curvature of an object side surface of the negative single lens cemented to the image pickup device, and reference character R01 denotes a radius of curvature of an image side surface of the negative first lens.

2. The magnifying endoscope optical system according to claim 1, wherein
the following conditional expression (4) is satisfied:

$$5 < fr/f01 < 68 \quad (4)$$

where, reference character f01 denotes a focal distance of the negative first lens.

3. A magnifying endoscope optical system comprising:
a negative single lens cemented to an image pickup device and a moving lens group, wherein
switching at least between a normal observation state and a proximity magnifying state can be made by moving the moving lens group;
the following conditional expressions (1) and (3) are satisfied:

$$-65<fr/fw<-2 \tag{1}$$

$$0.15<Tr/fw<1.7 \tag{3}$$

where reference character fr denotes a focal distance of the negative lens cemented to the image pickup device, reference character fw denotes a focal distance of the entire system in the normal observation state, and reference character Tr denotes the middle thickness of the negative single lens cemented to the image pickup device.

4. The magnifying endoscope optical system according to claim 3, wherein
the following conditional expression (4) is satisfied:

$$5<fr/f01<68 \tag{4}$$

where, reference character f01 denotes a focal distance of the negative first lens.

5. A magnifying endoscope optical system comprising, in order from the object side, a positive first group, a negative second group, a positive third group, and a negative fourth group, wherein
the fourth group has a negative single lens cemented to the image pickup device;
the negative single lens is a negative single lens with a concave surface directed to the object side; and
an image position is adjusted by varying the group interval between the third group and the fourth group, and focusing and magnification are made by moving only the second group on the optical axis;
switching at least between a normal observation state and a proximity magnifying state can be made by moving the second group; and
the following conditional expression (1) is satisfied:

$$-65<fr/fw<-2 \tag{1}$$

where reference character fr denotes a focal distance of the negative single lens cemented to the image pickup device, and reference character fw denotes a focal distance of the entire system in the normal observation state.

6. The magnifying endoscope optical system according to claim 5, wherein
the following conditional expressions (5) to (7) are satisfied:

$$1.2<dm/fw<2.4 \tag{5}$$

$$0.9<f4/f2<9.5 \tag{6}$$

$$-0.6<expi(w)/\Sigma d<-0.3 \tag{7}$$

where reference character dm denotes a moving amount of the second group, reference character f4 denotes a focal distance of the fourth group, reference character f2 denotes a focal distance of the second group, reference character expi(w) denotes an exit pupil position of a maximum image height actual ray in the normal observation state (wide angle end), and reference character $\Sigma d$ denotes the entire length of the optical system.

7. The magnifying endoscope optical system according to claim 6, wherein the following conditional expression (8) is satisfied:

$$-25<f4/f1<-2 \tag{8}$$

where reference character f1 denotes the focal distance of the first group.

8. The magnifying endoscope optical system according to claim 5, wherein
the following conditional expression (4) is satisfied:

$$5<fr/f01<68 \tag{4}$$

where, reference character f01 denotes a focal distance of the negative first lens.

* * * * *